United States Patent
Jansen et al.

(10) Patent No.: US 11,832,600 B2
(45) Date of Patent: Dec. 5, 2023

(54) INSECT DRINKING WATER SUPPLY

(71) Applicant: Protix B.V., Dongen (NL)

(72) Inventors: Jaco Jansen, Breda (NL); Willemijn Heleen Lever, Nijmegen (NL); Hendrikus Ant Schol, Waspik (NL); Raymond Joseph Leushuis, Alphen (NL)

(73) Assignee: Protix B.V., Dongen (NL)

( * ) Notice: Subject to any disclaimer, the term of this patent is extended or adjusted under 35 U.S.C. 154(b) by 13 days.

(21) Appl. No.: 17/615,592

(22) PCT Filed: Jun. 3, 2020

(86) PCT No.: PCT/NL2020/050353
§ 371 (c)(1),
(2) Date: Dec. 1, 2021

(87) PCT Pub. No.: WO2020/246876
PCT Pub. Date: Dec. 10, 2020

(65) Prior Publication Data
US 2022/0304289 A1    Sep. 29, 2022

Related U.S. Application Data

(60) Provisional application No. 62/857,851, filed on Jun. 6, 2019.

(30) Foreign Application Priority Data

Jun. 19, 2019 (NL) .................................. 2023340

(51) Int. Cl.
*A01K 67/033* (2006.01)

(52) U.S. Cl.
CPC ...... *A01K 67/033* (2013.01); *A01K 2227/706* (2013.01)

(58) Field of Classification Search
CPC ........................ A01K 67/033; A01K 2227/706
See application file for complete search history.

(56) References Cited

U.S. PATENT DOCUMENTS

| | | | |
|---|---|---|---|
| 2014/0020630 A1* | 1/2014 | Courtright | A01K 29/00 119/6.6 |
| 2019/0191678 A1* | 6/2019 | Alrayya | A23K 50/90 |
| 2021/0137137 A1* | 5/2021 | Leo | A23K 40/20 |

FOREIGN PATENT DOCUMENTS

| CN | 103651272 A | 3/2014 |
|---|---|---|
| CN | 105340843 A | 2/2016 |
| CN | 106172239 A | 12/2016 |

* cited by examiner

*Primary Examiner* — Monica L Perry
*Assistant Examiner* — Aaron M Rodziwicz
(74) *Attorney, Agent, or Firm* — N.V. Nederlandsch Octrooibureau

(57) ABSTRACT

An insect breeding device comprising at least one insect cage; a bin for holding drinking water or a tap for providing drinking water; a first pipe connected to the tap for receiving the drinking water, wherein the pipe is entering the at least one insect cage through a first opening; a nozzle, coupled to the first pipe, positioned inside the at least one insect cage configured to deliver the drinking water to the interior of the at least one insect cage; and a second pipe, coupled to a second opening, different from the first opening and located in the top wall of the cage or in a side wall of the cage, in the at least one insect cage, configured to deliver conditioned air into the at least one insect cage; and a third pipe, coupled to a third opening, different from the first and second opening and located in the top wall of the cage or in a side wall of the cage opposite to the second opening, in the at least one insect cage, configured to receive the conditioned air from the at least one insect cage.

20 Claims, 8 Drawing Sheets

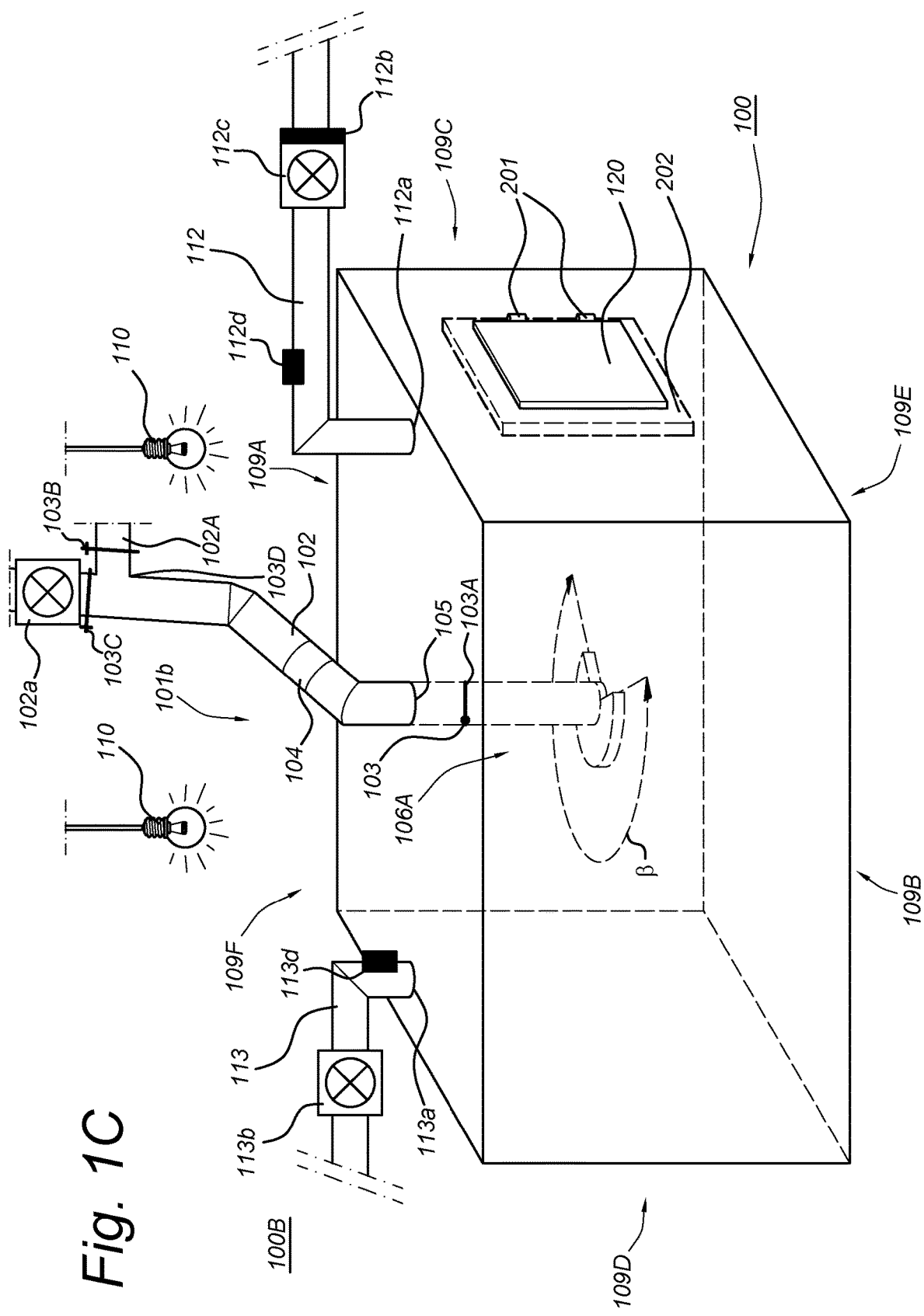

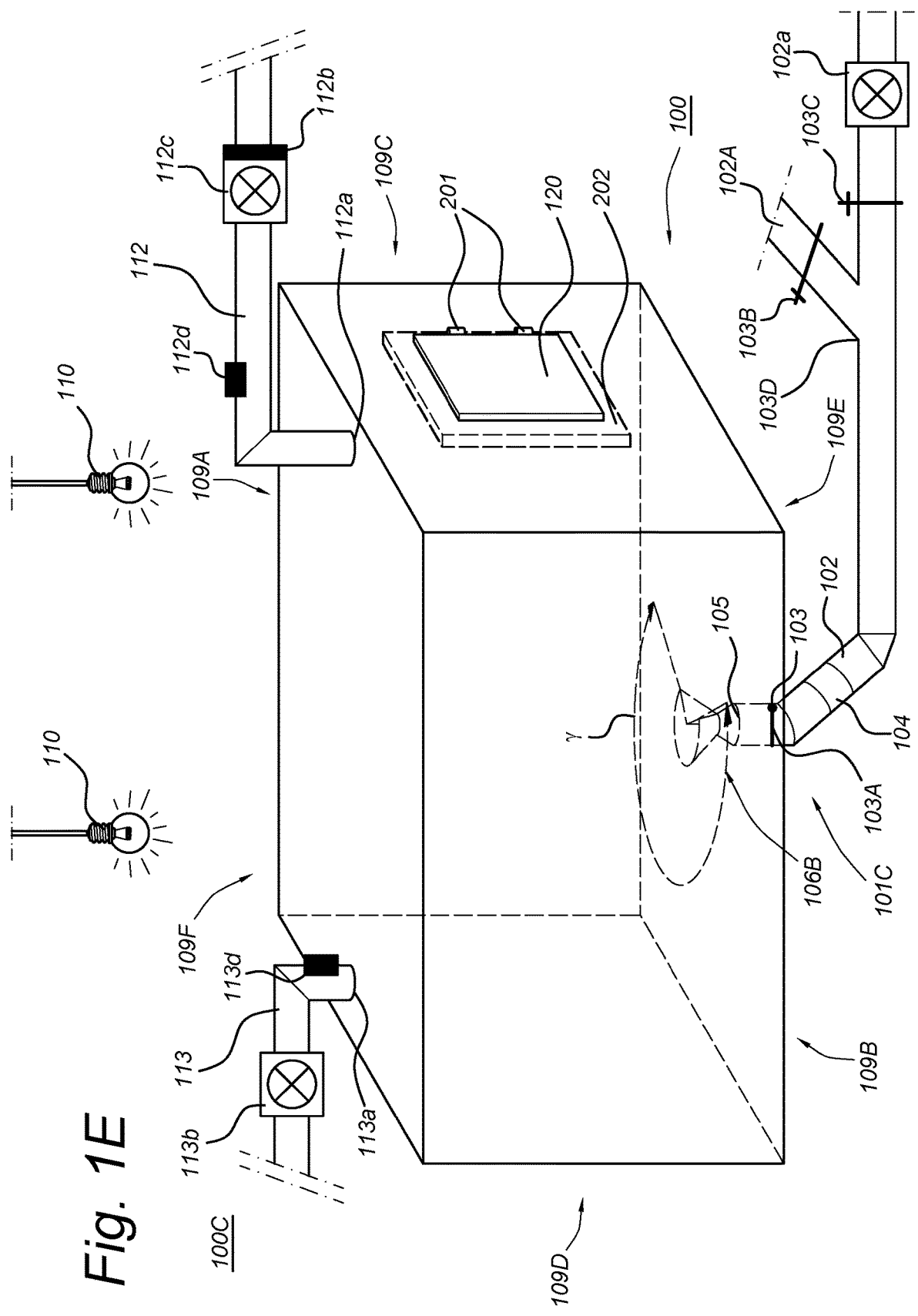

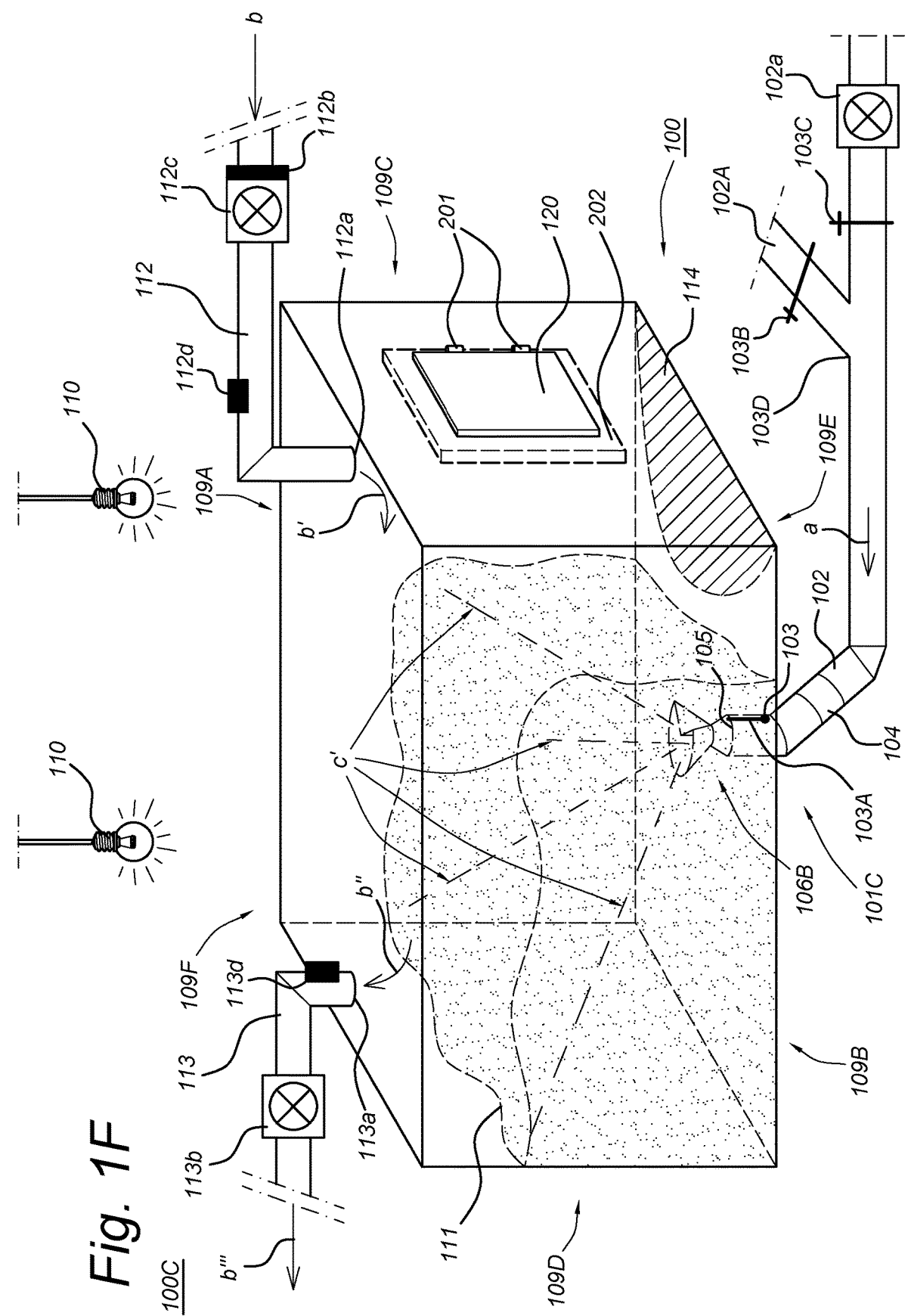

INSECT DRINKING WATER SUPPLY

TECHNOLOGICAL FIELD

The invention relates to an insect breeding device used for insect breeding. In particular, the invention relates to a cage for farming insects such as breeding insects, wherein the cage is provided with a drink water supply for insects.

BACKGROUND

Farming, i.e. rearing and breeding insects at an industrial and economically feasible scale is gaining momentum for its potential as an alternative source of animal lipids, fat, proteins, amino-acids, fatty acids, etc., compared to those currently provided by, for example, the livestock industry. However, bringing the current state of the art of insect farming, especially the breeding of insects, from a small scale to such an industrial scale poses challenges not encountered in small-scale insect research currently done in the laboratory. Known methods for farming insects are, for example, labor-intensive with at best a handful of aspects being automated.

One of the major drawbacks of scaling up a known insect breeding device is that there are no suitable methods or means for efficaciously providing the insects bred inside a cage comprised by the insect breeding with drinking water.

SUMMARY

It is an object of the invention to provide a solution to at least some of the aforementioned drawbacks of small-scale insect farming, especially the breeding of insects, in view of scaling up to a scale that is economically feasible.

In a first aspect of the invention this object is achieved by an insect breeding device comprising at least one insect cage, a source for providing insect drinking water, a first pipe connected to the source for receiving the drinking water, wherein the pipe is entering the at least one insect cage through a first opening in the at least one insect cage, a nozzle, coupled to the first pipe, positioned inside the at least one insect cage configured to deliver the drinking water to the interior surface of at least one of three of the four side walls, the top wall and a first portion of the bottom floor of the at least one insect cage, such that said interior surface of said at least one of three of the four side walls, the top wall and the first portion of the bottom floor is wetted with drinking water while leaving at least one of the fourth side wall and a second portion of the bottom floor of said at least one insect cage dry; and a second pipe, coupled to a second opening in the at least one insect cage, different from the first opening, in the top wall or in the fourth side wall of the at least one insect cage, configured to deliver gas such as air, preferably temperature conditioned air and/or relative air humidity-conditioned air, in the at least one insect cage, and a third pipe, coupled to a third opening in the at least one insect cage, different from the first and second opening, in the top wall or in the first side wall of the at least one insect cage opposite to the second opening, configured to pull or drain the gas such as air, preferably conditioned air, from the at least one insect cage.

An aspect of the present invention is an insect breeding device comprising
at least one insect cage, the insect cage having a bottom floor, a first side wall, a second side wall, a third side wall, a fourth side wall opposite to the first side wall and a top wall;
a water supply unit provided with:
a reservoir for providing a liquid;
a first pipe connected to the reservoir for receiving the liquid from the reservoir, wherein the first pipe is entering the at least one insect cage through a first opening in the at least one insect cage;
a nozzle, coupled to the first pipe, positioned inside the at least one insect cage configured to deliver the liquid to the interior of the at least one insect cage on at least one of the first side wall, the second side wall, the third side wall, the top wall and a first portion of the bottom floor apart from a second bottom floor portion, which second bottom floor portion is located adjacent to the fourth side wall.

An aspect of the present invention relates to an insect breeding device comprising at least one insect cage, the insect cage having a bottom floor, a first side wall, a second side wall, a third side wall, a fourth side wall opposite to the first side wall and a top wall; a water supply unit provided with: a reservoir for providing a liquid; a first pipe connected to the reservoir for receiving the liquid from the reservoir, wherein the first pipe is entering the at least one insect cage through a first opening in the at least one insect cage; a nozzle, coupled to the first pipe, positioned inside the at least one insect cage configured to deliver the liquid to the interior of the at least one insect cage on at least one of the surface of the first side wall, the second side wall, the third side wall, preferably all three surfaces of the first, second and third side wall, and optionally at least a portion of the surface of the top wall and optionally a first portion of the surface of the bottom floor. Preferred is the insect breeding device of the invention, wherein the nozzle is configured to deliver the liquid to the interior of the at least one insect cage on at least one of the surface of the first side wall, the second side wall, the third side wall, preferably all three surfaces of the first, second and third side wall, and optionally at least a portion of the surface of the top wall, and optionally a first portion of the surface of the bottom floor apart from a second bottom floor portion, which second bottom floor portion is located adjacent to the fourth side wall. Herewith, when the nozzle is expelling water into the interior of the at least one insect cage, the fourth side wall remains dry, i.e. is not wetted with liquid expelled through the nozzle, and in addition, at least the second portion of the surface of the bottom floor adjacent to the fourth side wall also remains dry when the water supply unit is supplying the nozzle with liquid, preferably water, more preferably demineralized water.

An embodiment is the insect breeding device according to the invention, wherein the nozzle is configured to deliver liquid on at least the first side wall, the second side wall \and the third side wall.

An embodiment is the insect breeding device according to the invention, wherein the liquid is water, preferably demineralized water.

An embodiment is the insect breeding device according to the invention, wherein the fourth side wall of the at least one insect cage is provided with a cage access opening for receiving an ovisite, and is provided with an openable door covering said cage access opening and the ovisite, if present, when said door is in closed position, wherein the ovisite is positioned above the bottom floor portion of the bottom floor of the at least one insect cage, such that during operation of the water supply unit the ovisite is likewise as that bottom floor portion also outside the reach of water jets delivered by the nozzle.

This arrangement enables efficient provision of the one or more insect cages with insect drinking water, while leaving a portion of the inner surface of the cage dry, since the drinking water enters the insect cage(s) upon being sprayed to a portion of the interior cage surface via the nozzle, therewith wetting said surface portion with water droplets sufficiently small in size that these droplets will stay adhered to the surface without flowing downward and without accumulating into pools of water, e.g. at the bottom floor.

An embodiment is the insect breeding device according to the invention, wherein the at least one insect cage is provided with a second pipe connected to a supply of conditioned air for receiving the conditioned air and for delivery of the conditioned air inside the insect cage during operation of the insect breeding device, the second pipe connected to a second opening in the top wall in the proximity of the fourth side wall, or in the fourth side wall, of the at least one insect cage, and the second pipe provided with an air conditioning unit for conditioning of the air temperature and the relative humidity of the air before delivery of the conditioned air inside the at least one insect cage during operation of the insect breeding device, and a first driver for transport and delivery of the conditioned air through second pipe and inside the at least one insect cage; and wherein the at least one insect cage is provided with a third pipe for receiving the conditioned air delivered by second pipe during operation of the insect breeding device, connected to a third opening in the top wall in the proximity of the first side wall, or in the first side wall, of the at least one insect cage, the third pipe optionally provided with a second driver for pulling conditioned air through the at least one insect cage during operation of the insect breeding device. The second opening in the top wall 'in the proximity of the fourth side wall' and the third opening in the top wall 'in the proximity of the first side wall', should be understood as the openings being located in the top wall of the insect cage, near the fourth side wall and near the first side wall, respectively. For example the second and third openings are located in the top wall at a distance of between 0% and 15% from the fourth side wall, respectively the first side wall, measured from the top side of the front fourth side wall and first side wall, respectively. For example the second opening is located in the top wall at a distance of between 0% and 15% from the fourth side wall measured from the top side of the fourth side wall, and at a distance of between 0% and 15% from one of the second and third side walls adjacent to the fourth side wall, measured from the top side of either the second side wall or the third side wall. For example the third opening is located in the top wall at a distance of between 0% and 15% from the first side wall measured from the top side of the first side wall, and essentially in the middle between the top side of the second side wall and the top side of the third side wall.

The air inlet opening coupled to the second pipe and the air outlet opening coupled to the third pipe allow for control of the temperature and of the relative humidity of the air inside the cage by blowing conditioned air through the cage, the air having a set temperature and a set relative air humidity such that water droplets at the wetted inner surface portion of the cage remain for a predetermined time (during farming of the insects inside the cage), or evaporate, depending on the temperature and relative air humidity parameters set for the conditioned air.

During breeding of insects such as black soldier flies availability of drinking water to the insects is essential for the successful emerging of insect pupae provided in the cage, i.e. at the non-wetted and dry second portion of the bottom floor of the cage, the subsequent mating of male and female flies, and ovipositioning (laying of eggs) by the gravid female flies at a desired ovisite (position in the cage for receiving eggs) located at the non-wetted and dry fourth side wall of the insect cage or at the non-wetted and dry second portion of the bottom floor of the cage. However, insects should not die by drowning in too large water droplets, i.e. in water pools, for example located at the bottom floor of the cage or at the surface walls of the cage. In addition, pupae delivered in the cage should not be wetted with the drinking water, in order to prevent dying of the pupae, rotting of the pupae, both resulting in evolvement of a smell functioning as an undesired hot spot for ovipositioning by the gravid female insects. This induces losses of insect eggs since harvesting of the eggs is prevented and less eggs will accumulate in the removable ovisite. In addition, presence of water droplets or even pools of water too large in volume or depth for flies to survive when entering such water reservoir, results in fly carcasses, such carcasses spreading a smell serving as an olfactory attractant for the gravid female flies. As a result, the flies oviposition at the location of dead flies, and not in the ovisite, again hampering efficient egg collection at high yield. Moreover, presence of pupae carcasses and/or fly carcasses from an early stage of an insect breeding cycle, e.g. from the first hour to the first day onwards, up to for example the end of day 2 or 3, in the insect cage hinders quick and efficient cleaning of the interior of the cage after the breeding cycle is terminated. Therefore, occurrence of fly carcasses and/or pupae carcasses at the start and during the early stage of a breeding cycle, upon wetting pupae or upon provision of too large water pounds in the cage, inducing dying of pupae and drowning of flies, should be avoided. The operation of the insect breeding device of the invention provides for optimized insect breeding conditions, preventing these drawbacks of wetting pupae and drowning flies. Furthermore, the ovisite should not be wetted during the breeding cycle of insects including the ovipositioning of gravid female flies in the ovisite, since wetting of the ovisite with drinking water can damage the laid eggs, induce a risk for rotting of the eggs, and/or may provide a substrate for undesired growth of mould, yeast, bacterium, etc., destroying the harvest. Since operation of the insect breeding device of the invention prevents the spraying of drinking water in the direction of the fourth side wall of the at least one cage, wherein said fourth side wall provides the surface onto which the ovisite is positioned, the ovisite remains dry and the aforementioned drawbacks and risks when wetting the ovisite and the eggs laid therein, are not occurring, according to the invention.

As said, having clean cages for breeding insects is a prerequisite for successful egg harvesting, and therefore there is a need to provide a clean insect cage at the start of the insect breeding cycle when re-using the cages from a previous insect breeding cycle, the cage remaining as clean as possible during the breeding cycle. Gravid female insects, such as black soldier flies, are tempted to lay eggs (referred to as "ovipositioning") in the vicinity of or in any suitable food source for the eggs to hatch. The olfactory attractant emerging from exuvia and dead insects stimulate the gravid flies to oviposition in areas of the cage other than at the desired location for ovipositioning (laying eggs), i.e. the "ovisite". Thus, the most likely consequence of wetting ovisites and eggs and pupae and pupae remains in the cage is sub-optimal egg collection. In addition, accumulation of wetted larvae remains, dead larvae, and wetted eggs in the cages also introduces the risk of emerging diseases, growth of microbes such as bacteria, yeasts and mold, for adversely influencing the insect colony.

An embodiment is the insect breeding device according to the invention, wherein the at least one insect cage is provided with a second pipe connected to a supply of conditioned air for receiving the conditioned air and for delivery of the conditioned air inside the insect cage during operation of the insect breeding device, the second pipe connected to a second opening in the top wall in the proximity of the fourth side wall, or in the fourth side wall, of the at least one insect cage, and the second pipe provided with an air conditioning unit for conditioning of the air temperature and the relative humidity of the air before delivery of the conditioned air inside the at least one insect cage during operation of the insect breeding device, and a first driver for transport and delivery of the conditioned air through second pipe and inside the at least one insect cage; and wherein the at least one insect cage is provided with a third pipe for receiving the conditioned air delivered by second pipe during operation of the insect breeding device, connected to a third opening in the top wall in the proximity of the first side wall, or in the first side wall, of the at least one insect cage, the third pipe optionally provided with a second driver for pulling conditioned air through the at least one insect cage during operation of the insect breeding device.

An embodiment is the insect breeding device according to the invention, wherein during operation of the insect breeding device the first driver pumps between 10 m$^3$/hour and 200 m3/hour conditioned air inside the at least one insect cage, preferably about 100 m$^3$/hour, more preferably about 45 m$^3$/hour. An embodiment is the insect breeding device according to the invention, wherein the first driver is configured to pump between 10 m$^3$/hour and 200 m$^3$/hour conditioned air inside the at least one insect cage, such as 25 m$^3$/hour-150 m$^3$/hour, preferably about 100 m$^3$/hour, more preferably about 45 m$^3$/hour.

An embodiment is the insect breeding device according to the invention, wherein the temperature of the conditioned air is 29° C.-35° C., preferably 30° C.-34° C., more preferably 31° C.-32.5° C., and/or the relative air humidity of the conditioned air is 45%-90%, preferably 47%-84%, more preferably 48.5%-74.5%. An embodiment is the insect breeding device according to the invention, wherein the temperature of the conditioned air is 25° C.-37° C., preferably 30° C.-34° C., more preferably 31° C. — 32.5° C., and/or wherein the relative air humidity of the conditioned air is 45%-90%, preferably 47%-84%, more preferably 48.5%-74.5%, when the temperature of the conditioned air is 29° C.-35° C., preferably 31° C.-32.5° C. Thus for example, the temperature of the conditioned air is between 31.5° C. and 32° C. and the relative humidity of the air is between 48.5% and 74.4%.

An embodiment is the insect breeding device according to the invention, wherein the air conditioning unit is an absolute air humidity control unit which is configured to controllably provide the at least one insect cage with an air flow b' of conditioned air through the cage(s) with an absolute air humidity of between 5 gram H$_2$O/kg air and 46 gram H$_2$O/kg air at an air temperature of between 25° C. and 38° C. at atmospheric pressure of 1.0 bar, preferably an absolute air humidity of between 10 gram H$_2$O/kg air and 30 gram H$_2$O/kg air at an air temperature of between 28° C. and 35° C., preferably between 29° C. and 34° C., more preferably between 31° C. and 33° C., at atmospheric pressure of 1.0 bar. These settings for the temperature and the air humidity inside the insect cage are for example suitable for breeding insects such as black soldier fly.

An embodiment is the insect breeding device according to the invention, wherein the insect breeding device is provided with at least one light source located above the top wall of the at least one insect cage. The provision of a light source, e.g. a controllable light source allows for insect breeding independent from availability of day light, sun light. Light-dark cycles are controllable with the provision of a light source, and therewith the breeding of the insects inside the cage comprised by the insect breeding device is optimizable. Similar, the light color and/or light intensity during (subsequent) cycles of light/dark can be selected and set at a predetermined wavelength and intensity. These parameters can further contribute to optimized insect breeding. Provision of the light source above the insect cage furthermore is beneficial for breeding insects in that the risk for insects becoming drown in water droplets that may occasionally be present at the bottom floor of the insect cage, is reduced, or even the drowning of insects in water droplets is prevented, since insects such as adult black soldier flies prefer to locate near the source of light, i.e. here in the top portion of the interior of the cage (portion of the side walls adjacent to the top wall, and at or near the top wall).

It is preferred that the insect breeding device further comprises a gas drying apparatus comprising a ventilator and a heater for generating a heated gas flow; the gas drying apparatus coupled to the second pipe coupled to the second opening of the insect cage for heating the conditioned air that is delivered through said second pipe inside the at least one cage. At the end of a breeding cycle wherein insects are bred in the at least one insect cage, the drinking water supply through the first pipe and first opening is terminated and the cage is dried by blowing gas such as air such as heated air through the at least one insect cage, by delivering the heated air through the second pipe and second opening, wherein the heated air is removed from the cage through the third opening and third pipe, located in the opposite side of the cage, either in the top wall, or in the first side wall opposite the fourth side wall.

An embodiment is the insect breeding device according to the invention, wherein the nozzle is provided with three arms oriented in a plane (see FIG. 1A, B, FIG. 3A, 3B), the three arms defining angles of 45°-120°, preferably 90° between a first arm and a second arm, preferably the second arm pointing to the first side wall, and between the second arm and a third arm and an angle of 120°-270°, preferably 180° between the first arm and the third arm pointing to the fourth side wall (which comprises an ovisite, i.e. an egg receiver/egg holder), each of the three arms having a fluid exit opening, the nozzle configured to deliver water jets in directions a1, a2, a3 over an angle α, δ of 120°-315°, preferably between 180° and 270° during operation of the insect breeding device, such that the water jets wet the first side wall, the second side wall and the third side wall of the at least one insect cage; or wherein the nozzle is a semi-circular disc nozzle covering 180° of a circular disc nozzle, or a three-quarter circular disc nozzle covering 270° of a circular disc nozzle (See FIG. 1C, D), the nozzle configured to deliver water jets in directions c over an angle β, δ of 180°-270°, preferably 180° for the semi-circular disc nozzle and 270°-315°, preferably 270° for the three-quarter circular disc nozzle during operation of the insect breeding device, such that the water jets wet the first side wall, the second side wall and the third side wall of the at least one insect cage (and not the fourth side wall opposite to the first side wall); or wherein the nozzle is a semi-circle conical nozzle covering 180° of a conical nozzle, or a three-quarter circle conical nozzle covering 270° of a conical nozzle (see FIG. 1E, F), the nozzle configured to deliver water jets in directions c' over an angle δ, γ of 180°-270°, preferably 180° for the semi-circle conical nozzle and 270°-315°, preferably 270° for the three-quarter circle conical nozzle during operation of the insect breeding device, such that the water jets wet the first side wall, the second side wall and the third side wall and optionally the top wall of the at least one insect cage (leaving the fourth side wall dry). It is to be understood that the three-quarter circular disc nozzle (see FIG. 1C) may also cover 120°-315° of a full circular disc nozzle, but about 270° is preferred. It is to be understood that the three-quarter circle conical nozzle (see FIG. 1E) may also cover 120°-315° of a full circular conical nozzle, but about 270° is preferred. It is part of the invention that the nozzle inside the insect cage is configured such that at least (a portion of) one of the first side wall, second side wall, third side wall is at least partially wetted when the water supply unit is in operation, preferably all three of the first, second, third side wall of the insect cage are at least partially wetted, and in addition optionally the portion of the bottom floor outside the bottom floor portion 114 that remains dry during operation of the water supply unit (see FIG. 1B, D, F, FIG. 2, FIG. 3A, B; area 114), is at least partially wetted when the water supply unit is in operation, and optionally at least a portion of the top wall is wetted when the water supply unit is in operation, and optionally the portion of the fourth side wall outside the cage access opening for receiving an ovisite and outside the provided ovisite therein, is at least partially wetted when the water supply unit is in operation.

An embodiment is the insect breeding device according to the invention, wherein the first pipe of water supply unit is provided with a third driver and a first valve positioned downstream from the third driver when a flow of liquid towards the at least one insect cage during operation of the water supply unit is considered, and wherein the first pipe is further provided with a branching opening connected to branch pipe, the branching opening positioned downstream from the first valve when a flow of liquid towards the at least one insect cage during operation of the water supply unit is considered, wherein branch pipe comprises a second valve. The branching opening is positioned upstream from the nozzle when a flow of liquid towards the at least one insect cage during operation of the water supply unit is considered.

An embodiment is the insect breeding device according to the invention, wherein the first pipe is provided with a third valve which is configured such that during operation of water supply unit the third valve opens when the first valve is in open position and the second valve is in closed position, and the third valve closes when the first valve is in closed position and the second valve is in open position. An embodiment is the insect breeding device according to the invention, wherein the third valve is a spring valve. An embodiment is the insect breeding device according to the invention, wherein the first pipe is provided with a spring valve pivotally connected with the interior side of the first pipe via pivot, the spring valve configured such that during operation of water supply unit the spring pivotally opens the first pipe in the direction from the proximal end of the first pipe relative to the third driver to the distal end of the first pipe where nozzle is connected with the first pipe, when the first valve is in open position and the second valve is in closed position, such that liquid is delivered inside the at least one insect cage. Provision of the water supply unit comprised by the insect breeding device with a third valve located prior to the nozzle (FIG. 1A, C, E) when the stream of water running through the first pipe and towards the at least one insect cage during operation of the water supply unit is considered, is beneficial for the breeding of insects inside the insect cage comprised by the insect breeding device, in that when the water supply unit is not providing water to the nozzle, i.e. is not actively driving water towards the insect cage upon operation of the third driver, the nozzle is prevented from leaking water inside the cage. Preventing leakage of water into the interior of the insect cage prevents bred insects from becoming hit by water droplets and/or becoming drown in water droplets, which improves breeding efficiency since insects remain alive.

An embodiment is the insect breeding device according to the invention, wherein the spring valve is configured to open, when in closed position, when a liquid pressure in the first pipe of at least 4 bar is exerted onto the closed spring valve, and to close, when in open position, when a liquid pressure in the first pipe of 3.5 bar or less is exerted onto the open spring valve, during operation of the water supply unit.

An embodiment is the insect breeding device according to the invention, wherein the third driver is a third pump configured to provide liquid in the first pipe at a pressure of at least 4.5 bar, in particular 5-6 bar, during operation of the water supply unit, when the first valve is in open position and the second valve is in closed position.

An embodiment is the insect breeding device according to the invention, wherein the surface area of the cross section of the second pipe is such that during operation of the water supply unit the liquid pressure in the first pipe is less than 2 bar, in particular 0.8 to 1.2 bar, more in particular atmospheric pressure (about 1 bar), when the first valve is in closed position and the second valve is in open position, such that the third valve, e.g. the spring valve is in closed position.

An embodiment is the insect breeding device according to the invention, wherein the first pipe is provided with a first pressure gauge in a portion of the first pipe defined between the first valve and the spring valve.

An embodiment is the insect breeding device according to the invention, wherein the water supply unit is further provided with a sensor system comprising a first sensor provided to the second pipe and suitable for measuring air humidity in the conditioned air in air flow b' provided to the insect cage and entering said insect cage through second opening, and comprising a second sensor provided to the third pipe and for measuring air humidity in air flow b" of the conditioned air exiting the insect cage through third opening, the first sensor and the second sensor both connected to the first valve and to the second valve and to the third valve and optionally to the third driver, for controlling the first valve, the second valve, the third valve and optionally the third driver, or the first sensor and the second sensor both connected to the first valve, to the second valve and optionally to the third driver, when the third valve is a spring valve, for controlling the first valve, the second valve and optionally the third driver.

An embodiment is the insect breeding device according to the invention, comprising at least one insect cage, wherein the sensor system is configured to maintain the relative air humidity of the conditioned air in the at least one insect cage at a predetermined and constant value, or to maintain the absolute air humidity at an air temperature of between 25° C. and 38° C. and at atmospheric pressure of 1.0 bar of the conditioned air in the at least one insect cage, at a predetermined and constant value. If the second sensor senses an air humidity in air flow b" that is lower than the air humidity sensed by the first sensor in air flow b', the sensor system of the insect breeding device opens the first valve, closes the second valve, switches the third driver on (if not constantly kept on during breeding of insects) and opens the third valve, if the third valve is not a spring valve, such that the nozzle inside the insect cage is provided with water and the water is distributed over at least a side wall of the interior of the cage. This way, air humidity inside the insect cage increases and when the second sensor senses an air humidity in air flow b" that is essentially the same as the air humidity sensed by the first sensor in air flow b', the sensor system closes the first valve, opens the second valve, optionally switches off the third driver, and closes the third valve when the third valve is not a spring valve. The air humidity sensed by the first sensor is determined by the predetermined and selected air humidity value provided by the air conditioning unit (being it a preset value for the relative air humidity of the conditioned air provided by the air conditioning unit or being it a preset value for the absolute air humidity at an air temperature of between 25° C. and 38° C. and at atmospheric pressure of 1.0 bar of the conditioned air provided by the air conditioning unit). The air humidity senses by the first sensor is preset at a value that is optimal for breeding of insects such as adult black soldier fly. Typically, the temperature of the conditioned air is 25° C.-37° C., preferably 30° C.-34° C., more preferably 31° C.-32.5° C., and typically the relative air humidity of the conditioned air is 45%-90%, preferably 47%-84%, more preferably 48.5%-74.5%, when the temperature of the conditioned air is 29° C.-35° C., preferably 31° C.-32.5° C. Thus for example, the temperature of the conditioned air is between 31.5° C. and 32° C. and the relative humidity of the air is between 48.5% and 74.4%. Typically, the absolute air humidity is between 5 gram $H_2O$/kg air and 46 gram $H_2O$/kg air at an air temperature of between 25° C. and 38° C. at atmospheric pressure of 1.0 bar, preferably the absolute air humidity is between 10 gram $H_2O$/kg air and 30 gram $H_2O$/kg air at an air temperature of between 28° C. and 35° C., preferably between 29° C. and 34° C., more preferably between 31° C. and 33° C., at atmospheric pressure of 1.0 bar.

An embodiment is the insect breeding device according to the invention, wherein the at least one insect cage is a cluster of insect cages comprising two or more insect cages, such as 48-256 insect cages or multiples of 6, 12, 18, 24, 30, 36, 72 cages, wherein the first pipe of water supply unit comprises branch points each connected to water supply-unit branches, each water supply-unit branch comprising the third valve such as the spring valve and the nozzle located inside the individual insect cages, the insect breeding device further comprising a climate room enclosing the at least one insect cage and a portion of the water supply unit encompassing at least the portion of the first pipe comprising the branch points and the water supply unit branches.

An embodiment is the insect breeding device according to the invention, wherein the first pipe of the water supply unit comprises a second pressure gauge between the third driver and the first valve, and/or at least one vent downstream from the first valve and the second valve. The at least one vent is provided in a high portion of the first pipe that is at least locally positioned at a high point relative to portions of the first pipe immediately adjacent to said high portion of the first pipe, such that the first pipe is efficiently vented during operation of the water supply unit comprised by the insect breeding device of the invention. Presence of at least one vent, preferably at the highest location/position of the first pipe, relative to the horizontal, provides the ability to release the pipe from air that may occasionally be present and accumulate inside the first pipe, for example by entrance through the nozzle arm openings. Releasing the air from first pipe contributes to improved operation and stability of the water supply unit comprised by the insect breeding device. Delivery of a predetermined volume of water within a predetermined time window can be more accurate when building up of air in the first pipe is prevented.

An embodiment is the insect breeding device according to the invention, wherein the second pressure gauge further comprises
    a controller connected to the first valve and connected to the second valve and optionally connected to the third pump, wherein the controller is arranged to switch between a first state and a second state; wherein
        in the first state the first valve is closed, the second valve is open and the third pump is optionally switched off,
        in the second state, the first valve is open and the second valve is closed, and
    the third pump is switched on, if previously switched off.

An embodiment is the insect breeding device according to the invention, wherein the second pressure gauge further comprises
    a controller connected to the first valve and connected to the second valve and optionally connected to the third pump, wherein the controller is arranged to switch between a first state and a second state; wherein
        in the first state the first valve is closed, the second valve is open and the third pump is optionally switched off, such that the pressure in the first pipe is below 4 bar, e.g. about 1 bar,
        in the second state, the first valve is open and the second valve is closed, and the third pump is switched on, if previously switched off, such that the liquid pressure, preferably demineralized water pressure in the first pipe is higher than 4 bar, for example 5-7 bar, preferably between 4.5 bar and 6.5 bar such as between 5 bar and 6 bar. When the third valve is a spring valve, this spring valve is closed in the first state, since the spring valve only opens when a water pressure exceeding 4 bar is exerted onto the spring valve, such as 4.5 bar, 5 bar, 6 bar water pressure. When the third valve is a spring valve, this spring valve is opened in the second state, since the spring valve opens when a water pressure of at least 4 bar is exerted onto the spring valve, such as 4.5 bar, 5 bar, 6 bar water pressure.

An embodiment is the insect breeding device according to the invention, wherein the second pressure gauge further comprises a controller connected to the first valve, to the second valve, to the third valve and to the third pump, wherein the controller is arranged to switch between a first state and a second state; wherein in the first state the first valve and the third valve are closed, the second valve is open and the third pump is optionally switched off, such that the pressure in the first pipe is below 4 bar, e.g. about 1 bar; in the second state, the first valve and the third valve are open and the second valve is closed, and the third pump is switched on, if previously switched off.

An embodiment is the insect breeding device according to the invention, wherein the second pressure gauge further comprises a controller connected to the first valve, to the second valve, to the third valve and to the third pump, wherein the controller is arranged to switch between a first state and a second state; wherein in the first state the first valve and the third valve are closed, the second valve is open and the third pump is optionally switched off; in the second state, the first valve and the third valve are open and the second valve is closed, and the third pump is switched on, if previously switched off, such that the liquid pressure, preferably demineralized water pressure in the first pipe is higher than 4 bar, for example 5-7 bar, preferably between 4.5 bar and 6.5 bar such as between 5 bar and 6 bar.

An embodiment is the insect breeding device according to the invention, wherein the controller is further arranged to maintain the second state for a period between 300 milliseconds to 5000 milliseconds, such as between 500 milliseconds and 2500 milliseconds.

An embodiment is the insect breeding device according to the invention, wherein the controller is further arranged to maintain the first state for a period between 1 minute and 6 hours, preferably between 3 minutes and 3 hours, more preferably between 5 minutes and 2 hours.

An embodiment is the insect breeding device according to the invention, wherein the flow of liquid through the first pipe is between 10 L/min and 50 L/min, preferably between 15 L/min and 40 L/min, more preferably between 21 L/min and 25 L/min, when the first valve is open and the second valve is closed.

An embodiment is the insect breeding device according to the invention, wherein the at least one insect cage has a substantially block shape having rounded corners in the inner surface of the cage.

An embodiment is the insect breeding device according to the invention, wherein the at least one insect cage is manufactured using rotation molding of a polymer blend, preferably comprising polyethylene.

An embodiment is the insect breeding device according to the invention, the at least one insect cage is further configured to have inner dimensions of a width between 30 cm and 250 cm, a depth between 50 cm and 300 cm and a height between 10 cm and 160 cm, for example a width between 30 cm and 150 cm, a depth between 50 cm and 200 cm and a height between 10 cm and 60 cm.

The skilled person will appreciate that insect cages with any of the dimensions outside these ranges are also applicable for incorporation in the insect breeding device, as long as cleaning efficiency is sufficient. That is to say, an insect cage with larger dimension(s) may require a longer cleaning cycle period than 2-180 minutes, such as 240 minutes, and/or the volume of cleaning liquid is in the range of more than 500 liters per minute, such as 550-1000 liters per minute, and as a consequence, the second opening then has a cross-sectional surface area such that said second opening is arranged to drain a volume of cleaning liquid in the drainage range of over 500 liters per minute, as well. An embodiment is the insect breeding device according to the invention, wherein the first opening of the at least one insect cage is located in the bottom floor of the insect cage, or wherein the first opening of the at least one insect cage is located in the top wall of the insect cage.

For example, in an alternative embodiment, the insect breeding device according to the invention comprises the insect cages wherein the first opening is located in a side wall of the insect cage, in a portion of said side wall where the top wall and the side wall receiving the first pipe through the first opening, intersect, are suitable for space efficient stacking in the vertical direction. With the first opening provided in a side wall of the insect cage, the first pipe points sideward, therewith preventing space under or above the insect cage from being occupied by this first pipe. Typically, insect cages are stacked vertically such that adjacent insect cages in the vertical direction are spaced at between 5 cm and 40 cm, such as about 10 cm or 15 cm.

An embodiment is the insect breeding device according to the invention, wherein the nozzle is configured to have a spray angle between 180° and 270° and wherein the nozzle during operation of the water supply unit is configured to spray liquid in directions other than towards the fourth side wall of the at least one insect cage and is also configured to spray liquid in directions other than towards the bottom floor portion of the insect cage.

An embodiment is the insect breeding device according to the invention, wherein the nozzle is arranged to be positioned centrally in the inner volume of the at least one insect cage.

An embodiment is the insect breeding device according to the invention, wherein the at least one insect cage comprises a further nozzle, the nozzles being positioned off-center, in the inner volume of the at least one insect cage.

An embodiment is the insect breeding device according to the invention, wherein the insect breeding device comprises two insect cages stacked horizontally or vertically with each other.

An embodiment is the insect breeding device according to the invention, wherein the insect breeding device comprises two-eight hundred insect cages 100 stacked horizontally with each other, and/or two-fifteen insect cages 100 stacked vertically with each other, for example five-three hundred fifty horizontally stacked insect cages and/or three-seven vertically stacked insect cages.

BRIEF DESCRIPTION OF THE DRAWINGS

FIG. 1C illustrates a second embodiment of an insect breeding device of the present invention.

FIG. 1E illustrates a third embodiment of an insect breeding device of the present invention.

FIG. 1F illustrates the third embodiment of an insect cage of the present invention, as also displayed in FIG. 1E, but now showing the insect breeding advice when in operation, such that insect drinking water is distributed at a portion of the inner surfaces of the insect cage. The water is spread inside the cage through a conical nozzle wherein a cone segment of 45°-120°, preferably about 90° is omitted pointing in the direction of the side wall of the cage that remains dry and that comprises an ovisite.

DETAILED DESCRIPTION OF CERTAIN EMBODIMENTS

Figure 1A:
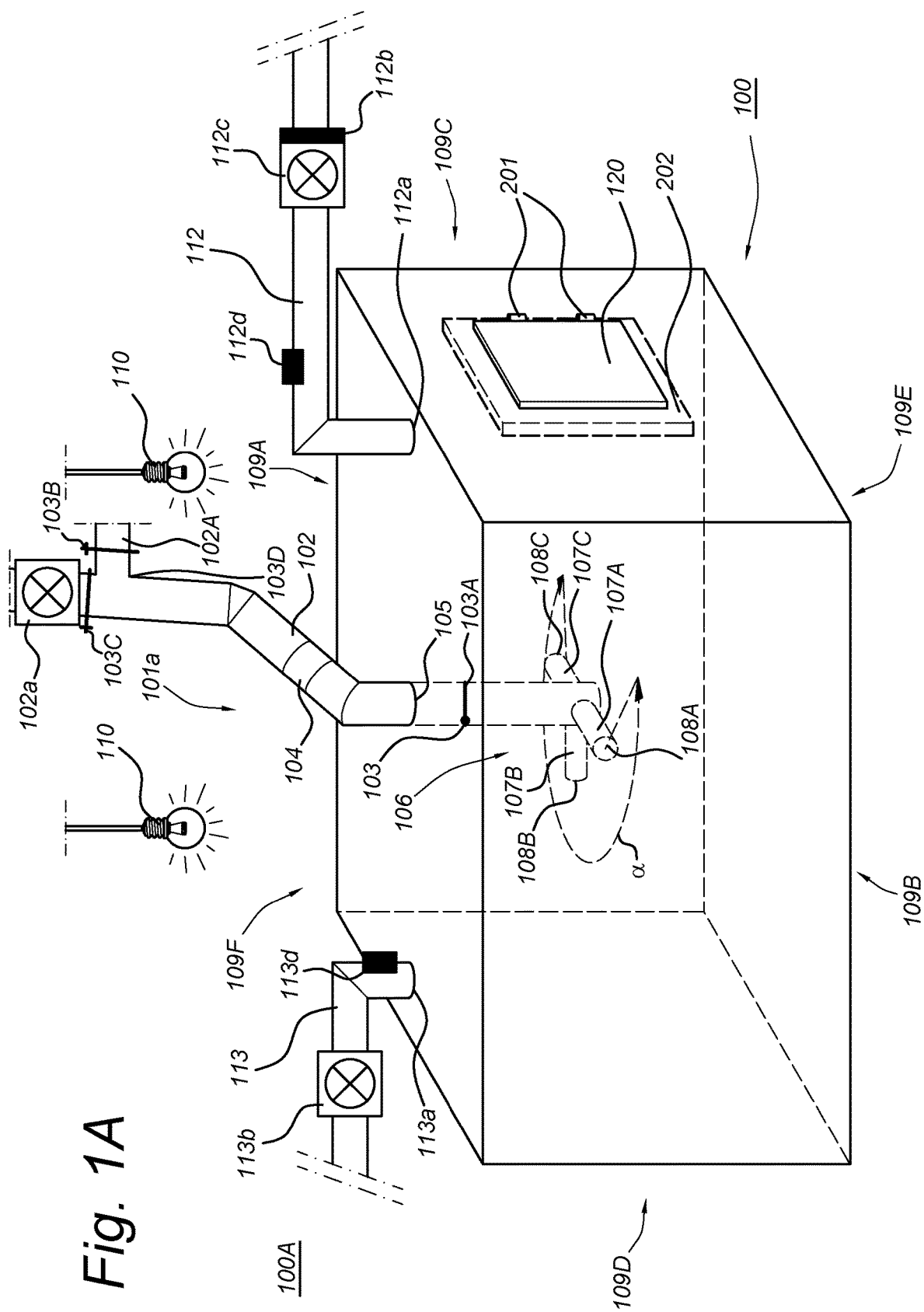
FIG. 1A illustrates a first embodiment of an insect breeding device of the present invention.
Figure 1B:
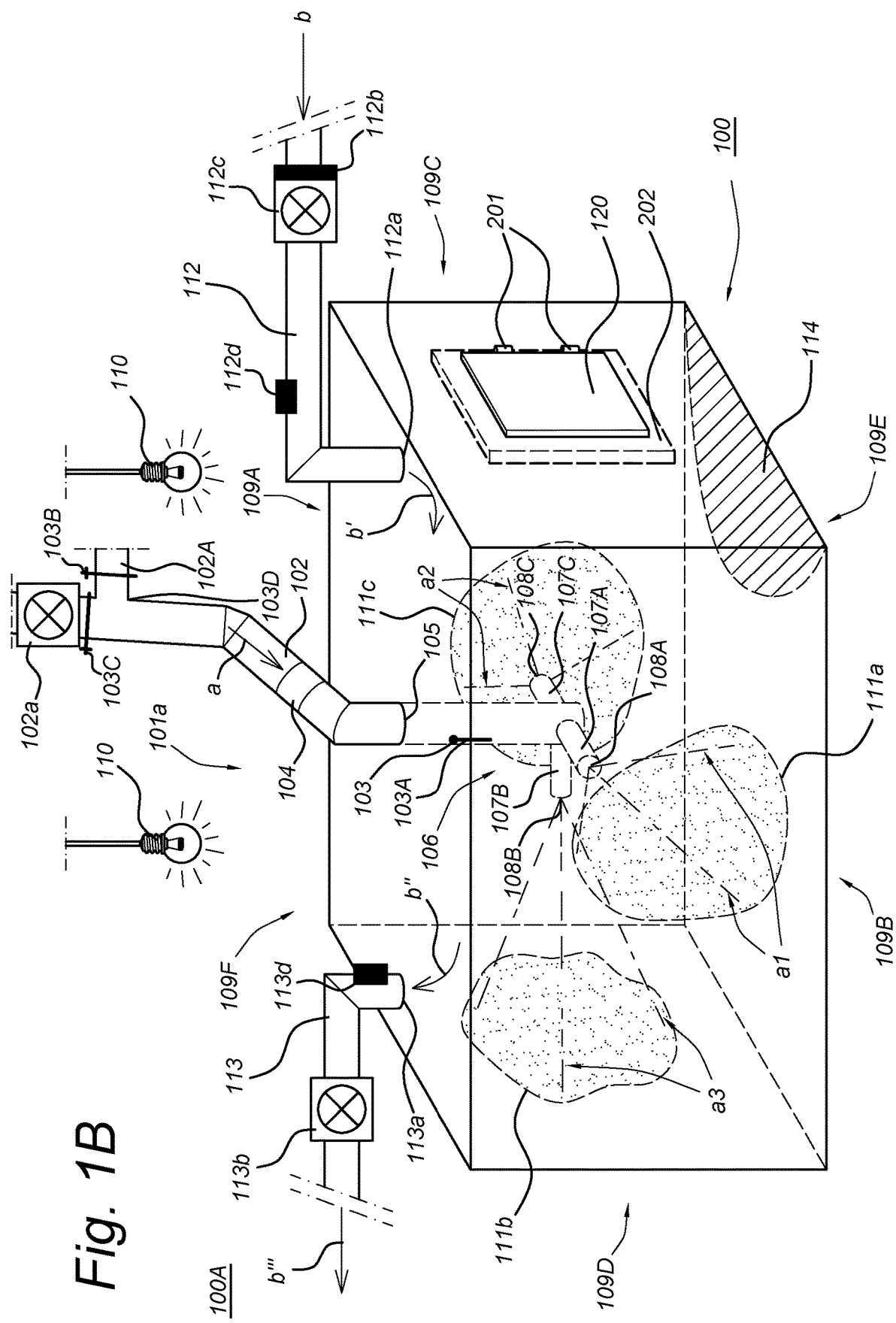
FIG. 1B illustrates the first embodiment of an insect cage of the present invention, as also displayed in FIG. 1A, but now showing the insect breeding advice when in operation, such that insect drinking water is distributed at a portion of the inner surfaces of the insect cage. The water is spread inside the cage through a cruciform nozzle wherein a branch of the cruciform is omitted at the side of the nozzle pointing to the side wall of the cage that remains dry and that comprises an ovisite in an opening of that side wall for receiving an ovisite.
Figure 1D:
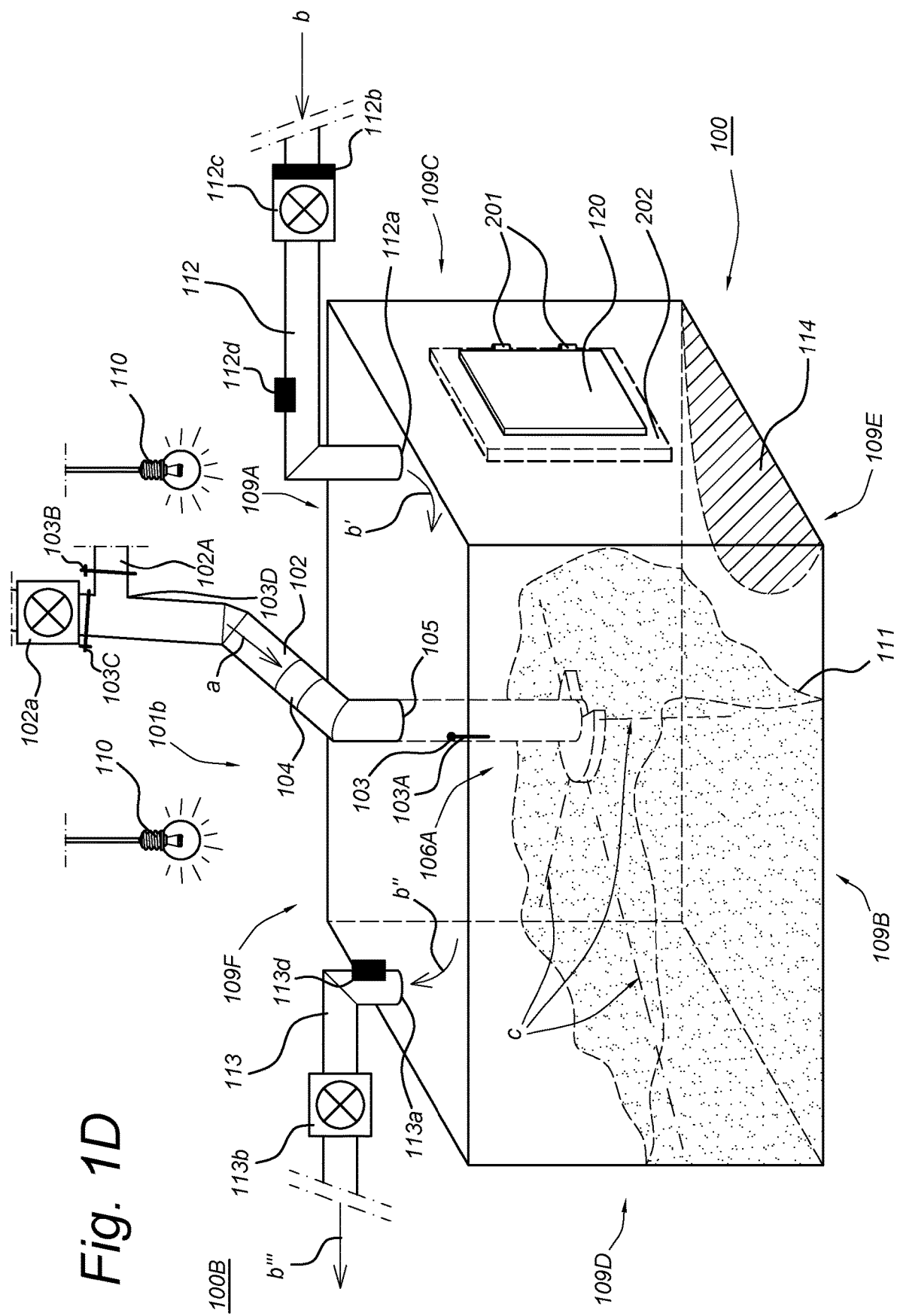
FIG. 1D illustrates the second embodiment of an insect cage of the present invention, as also displayed in FIG. 1C, but now showing the insect breeding advice when in operation, such that insect drinking water is distributed at a portion of the inner surfaces of the insect cage. The water is spread inside the cage through a circular nozzle wherein a circle segment of about 45°-120°, preferably about 90° is omitted pointing in the direction of the side wall of the cage that remains dry and that comprises an ovisite.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

The present invention is an insect breeding device that allows the breeding of insects in insect cages at a large scale. Use of the insect breeding device makes provision of the insect cage with insect drinking water by hand superfluous, i.e. demands less labor. Furthermore, with the insect breeding device of the invention, providing multiple insect cages with drinking water becomes controllable with regards to, for example, the volume of provided drinking water in the insect cages and the timing of the provision of drinking water to the insect cages, even optionally on a cage-by-cage basis. An important advantage of the insect breeding device of the invention is its applicability and suitability for use in provision of insect cages with drinking water, wherein the cages are impermeable for fluid, and applicability for industrial scale breeding of insects.

FIG. 1A and FIG. 1B, FIG. 1C and FIG. 1D, and FIG. 1E and FIG. 1F show the insect breeding device 100A, 100B, 100C, respectively, according to a first, second and third embodiment of the present invention, respectively. The insect breeding device 100A, 100B, 100C comprises an insect cage 100 in fluid connection with a drinking water supply unit comprising a first pipe connected to a drinking water supply or reservoir such as a tap or a container or a vessel containing the liquid, e.g. water, preferably demineralized water (FIG. 2), for supplying insect drinking water, here demineralized water. Although tap water would also suffice, applying demineralized water as the source of insect drinking water is preferred. Demineralized water limits the risk for clogging of tubes, linings, valves, shutters, taps, etc., since the risk for accumulation and precipitation of mineral salts on such surfaces and parts of a water circuit is reduced compared to when tap water would be applied. In addition, spreading droplets or a mist of demineralized water inside the cages such that the insects bred in the cages are provided with drinking water, does not result in precipitated traces of mineral salts once the demineralized water droplets are evaporated from the surface of the inside of the cages. This way, cleaning of insect cages of the insect breeding device after a breeding cycles is less laborious and takes less effort, time, energy and cleaning liquid for appropriately cleaning the inner side of the cages before a next round of insect breeding is initiated.

The term "demineralized water" has its regular scientific meaning and here refers to water from which all minerals are removed, if initially present.

An aspect of the invention is the insect breeding device 100A, 100B, 100C, 100D comprising
  at least one insect cage 100, the insect cage having a bottom floor 109E, a first side wall 109D, a second side wall 109A, a third side wall 109B, a fourth side wall 109C opposite to first side wall 109D and a top wall 109F;
  a water supply unit 101a, 101b, 101c, 500 provided with:
    a reservoir for providing a liquid;
    a first pipe 102, 102b connected to the reservoir for receiving the liquid from the reservoir, wherein the first pipe 102, 102b is entering the at least one insect cage 100 through a first opening 105 in the at least one insect cage;
    a nozzle 106, 106A, 106B, coupled to the first pipe 102, 102b, positioned inside the at least one insect cage 100 configured to deliver the liquid to the interior of the at least one insect cage 100 on at least one of the first side wall 109D, the second side wall 109A, the third side wall 109B, the top wall 109F and a portion of the bottom floor 109E apart from bottom floor portion 114, which bottom floor portion 114 is located adjacent to the fourth side wall 109C.

The insect cage 100 has a first, second and third side wall 109A, 109B, 109D of four side walls, a bottom floor 109E and a top wall 109F. The fourth side wall 109C is provided with an opening covered with a door 120 when the door is in the closed position. The insect cage is for example provided with an openable door 120, pivotally connected to the fourth side wall 109C. The door 120 provides access to an egg collector container 202, i.e. an ovisite 202, located inside the insect cage 100, and in the opening in the fourth side wall 109C. When present in the insect cage 100, the ovisite 202 has openings for receiving insect eggs laid by gravid insects such as gravid female black soldier flies, exposed to the interior side of the insect cage, i.e. pointing towards the third side wall 109D. Optionally, the insect breeding device is provided with at least one light source 110, positioned above the top wall 109F of insect cage 100.

A first pipe 102 is connected from the tap (not shown, connected to the driver 102a in FIG. 2) to the first opening 105 of the insect cage 100. A nozzle 106, 106A, 106B (for insect breeding devices 100A, 1008, 100C, respectively), coupled to the first pipe 102, is positioned inside the insect cage and is configured to deliver insect drinking water to the interior of the insect cage 100.

An embodiment is the insect breeding device 100A, 1008, 100C, 100D of the invention, wherein the nozzle 106, 106A, 106B is configured to deliver liquid on at least the first side wall 109D, the second side wall 109A and the third side wall 1098.

An embodiment is the insect breeding device 100A, 1008, 100C, 100D of the invention, wherein the liquid is water, preferably demineralized water.

An embodiment is the insect breeding device 100A, 1008, 100C, 100D of the invention, wherein the fourth side wall 109C of the at least one insect cage 100 is provided with a cage access opening for receiving an ovisite 202, and an openable door 120 covering said cage access opening and the ovisite 202, if present, when in closed position, wherein the ovisite 202 is positioned above the bottom floor portion 114 of the bottom floor 109E of the at least one insect cage 100, such that during operation of the water supply unit 101a, 101b, 101c, 500 the ovisite 202 is likewise as the bottom floor portion 114 also outside the reach of water jets a1, a2, a3, c, c' delivered by the nozzle 106, 106A, 106B. An embodiment is the insect breeding device 100A, 1008, 100C, 100D according to the invention, wherein the at least one insect cage 100 is provided with a second pipe 112 connected to a supply of conditioned air for receiving the conditioned air and for delivery of the conditioned air inside the insect cage 100 during operation of the insect breeding device 100A-D, the second pipe 112 connected to a second opening 112a in the top wall 109F in the proximity of the fourth side wall 109C, or in the fourth side wall 109C, of the at least one insect cage 100, and the second pipe 112 provided with an air conditioning unit 112b for conditioning of the air temperature and the relative humidity of the air before delivery of the conditioned air inside the at least one insect cage 100 during operation of the insect breeding device 100A-D, and a first driver 112c for transport and delivery of the conditioned air through second pipe 112 and inside the at least one insect cage 100; and wherein the at least one insect cage 100 is provided with a third pipe 113 for receiving the conditioned air delivered by second pipe 112 during operation of the insect breeding device 100A-D, connected to a third opening 113a in the top wall 109F in the proximity of the first side wall 109D, or in the first side wall 109D, of the at least one insect cage 100, the third pipe 113 optionally provided with a second driver 113b for pulling conditioned air through the at least one insect cage 100 during operation of the insect breeding device 100A-D.

An embodiment is the insect breeding device 100A, 100B, 100C, 100D according to the invention, wherein the temperature of the conditioned air is 29° C.-35° C., preferably 30° C.-34° C., more preferably 31° C.-32.5° C., and/or the relative air humidity of the conditioned air is 45%-90%, preferably 47%-84%, more preferably 48.5%-74.5%.

An embodiment is the insect breeding device 100A, 100B, 100C, 100D according to the invention, wherein the air conditioning unit 112b is an absolute air humidity control unit 112b which is configured to controllably provide the at least one insect cage 100 with an air flow b' of conditioned air through the cage(s) with an absolute air humidity of between 5 gram $H_2O$/kg air and 46 gram $H_2O$/kg air at an air temperature of between 25° C. and 38° C. at atmospheric pressure of 1.0 bar, preferably an absolute air humidity of between 10 gram $H_2O$/kg air and 30 gram $H_2O$/kg air at an air temperature of between 28° C. and 35° C., preferably between 29° C. and 34° C., more preferably between 31° C. and 33° C., at atmospheric pressure of 1.0 bar.

An embodiment is the insect breeding device 100A, 100B, 100C, 100D according to the invention, wherein the insect breeding device is provided with at least one light source 110 located above the top wall 109F of the at least one insect cage 100.

For insect breeding device 100A (FIG. 1A, B), the nozzle is a cruciform shaped nozzle for which one arm of the cruciform is omitted, leaving the cruciform shaped nozzle with arms 107A, 107B, 107C. This way, drinking water driven through pipe 102 and entering the nozzle 106 is dispensed inside the insect cage in three directions instead of four, when the drinking water exits the nozzle arms through openings 108A in the direction of the side wall 109B, 108B in the direction of the side wall 109D, 108C in the direction of the side wall 109A. That is to say, drinking water is not dispensed and pushed in the direction of the side wall 109C, such that the ovisite 202 is not covered and contacted with the drinking water, and therewith essentially stays dry during an insect breeding cycle. In addition, surface portion 114 of the bottom floor 109E is also not overlaid with drinking water due to the omitted arm of the cruciform nozzle. The surface portion 114 is located below the door opening covered by door 120. At the start of an insect breeding cycle, for example pupae such as for example pupae of black soldier fly, are introduced inside the insect cage by spreading those pupae over the surface portion 114 of the bottom floor 109E of the insect cage 100 comprised by the insect breeding device 100A, i.e. the surface portion that remains dry and is not covered with droplets or a mist of drinking water during operation of the water supply unit comprising a source of demineralized water such as a tap, and nozzle 106.

Embodiments are the insect breeding device 100A, 100B, 100C, 100D according to the invention, wherein the nozzle 106 is provided with three arms 107A, 107B, 107C oriented in a plane (FIG. 1A, B, FIG. 3A, B), the three arms defining angles of 90° between a first arm 107A and a second arm 107B and between the second arm 107B and a third arm 107C and an angle of 180° between the first arm 107A and the third arm 107C pointing to the fourth side wall 109C, each of the three arms 107A, 107B, 107C having a fluid exit opening 108A, 108B, 108C, the nozzle 106 configured to deliver water jets in directions a1, a2, a3 over an angle α, δ of between 180° and 270° during operation of the insect breeding device 100A-D, such that the water jets wet the first side wall 109D, the second side wall 109A and the third side wall 109B of the at least one insect cage 100; or wherein the nozzle 106A is a semi-circular disc nozzle covering 180° of a circular disc nozzle, or a three-quarter circular disc nozzle covering 270° of a circular disc nozzle (FIG. 1C, D), the nozzle 106A configured to deliver water jets in directions c over an angle β, δ of 180° for the semi-circular disc nozzle and 270° for the three-quarter circular disc nozzle 106A during operation of the insect breeding device 100A-D, such that the water jets wet the first side wall 109D, the second side wall 109A and the third side wall 109B of the at least one insect cage 100; or wherein the nozzle 106B is a semi-circle conical nozzle covering 180° of a conical nozzle, or a three-quarter circle conical nozzle 106B covering 270° of a conical nozzle (FIG. 1E, F), the nozzle 106B configured to deliver water jets in directions c' over an angle δ, γ of 180° for the semi-circle conical nozzle and 270° for the three-quarter circle conical nozzle 106B during operation of the insect breeding device 100A-D, such that the water jets wet the first side wall 109D, the second side wall 109A and the third side wall 109B and optionally the top wall 109F of the at least one insect cage 100.

Figure 3A:
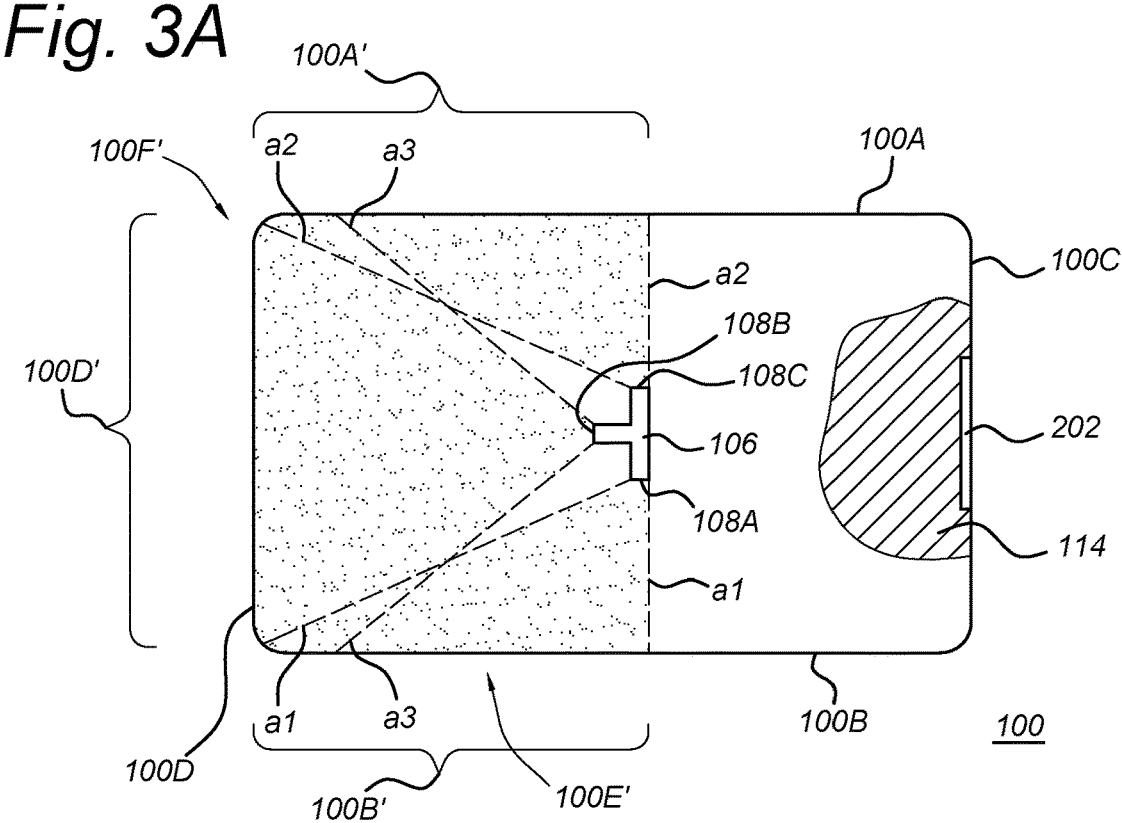
FIG. 3A and FIG. 3B show the portion of three of the four side walls and the bottom floor and the top side of an insect cage comprised by the insect breeding device of the invention, that is wetted when a water supply unit of the insect breeding device is operating and water is spread through the nozzle of the water supply unit. Here, the nozzle is a three-armed nozzle, wherein the nozzle arm openings point away from the side of the insect cage and point away from the bottom floor portion that both are intended to remain dry when the water supply unit is operating.

In FIG. 3A, a cross-section of the insect cage 100 is shown, in the direction from top to bottom, displaying the nozzle 106 (FIG. 1A, B). When in operation (water is flowing through first pipe 102 towards nozzle 106), the water supply unit (See FIG. 1, 2) provides water to the nozzle, the nozzle expelling the water along water streams a1 from nozzle arm opening 108A, water streams a2 from nozzle arm opening 108B, water streams a3 from nozzle arm opening 108C, in the direction of the location of the first, second, third side walls 100A, 100B, 100D of the insect cage 100, such that side wall portions 100A', 100B' and 100D' of the side walls 100A, 100B and 100D are wetted. Optionally, also bottom wall portion 100E' and/or top side portion 100F' is/are also wetted when the water supply unit is operating. The bottom floor portion 114 of bottom floor 100E remains dry when nozzle 106 is expelling water; the opening in the fourth side wall 100C for receiving ovisite 202 and the ovisite 202 when present, are also remaining dry when the water supply unit is operating. Portions of the side walls 100A, 100B, 100D, and at least portions of the bottom floor and the top side of the insect cage 100 remain dry when the water supply unit is operating and the nozzle is expelling water into the interior of the insect cage.

Figure 3B:
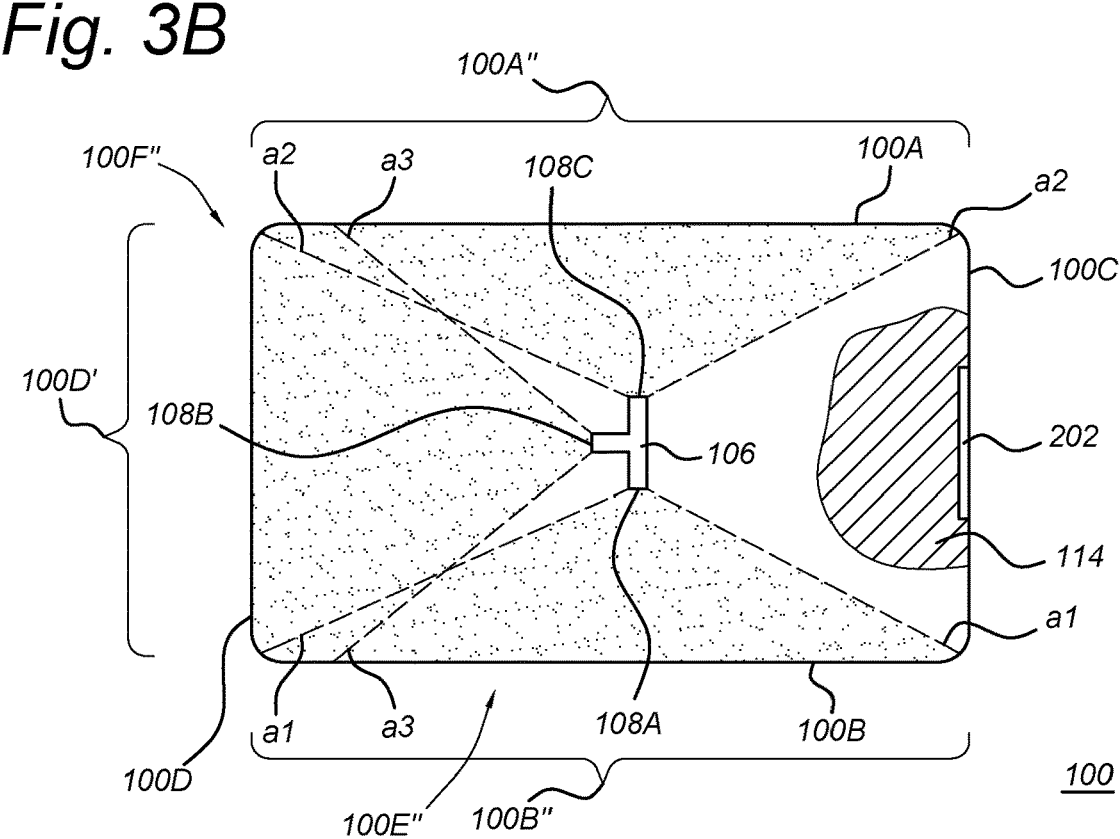

In FIG. 3B, a cross-section of the insect cage 100 is shown, in the direction from top to bottom, displaying the nozzle 106 (FIG. 1A, B). When in operation (water is flowing through first pipe 102 towards nozzle 106), the water supply unit (See FIG. 1, 2) provides water to the nozzle, the nozzle expelling the water along water streams a1 from nozzle arm opening 108A, water streams a2 from nozzle arm opening 108B, water streams a3 from nozzle arm opening 108C, in the direction of the location of the first, second, third side walls 100A, 100B, 100D of the insect cage 100, such that side wall portions 100A", 100B" and 100D' of the side walls 100A, 100B and 100D are wetted, which side wall portions essentially cover most or all of the inner surface of said side walls 100A, 100B, 100D. Optionally, also bottom wall portion 100E" and/or top side portion 100F" is/are also wetted when the water supply unit is operating. The bottom floor portion 114 of bottom floor 100E remains dry when nozzle 106 is expelling water; the opening in the fourth side wall 100C for receiving ovisite 202 and the ovisite 202 when present, are also remaining dry when the water supply unit is operating. Portions of the bottom floor 100E (FIG. 1) and the top side (FIG. 1) of the insect cage 100 thus remain dry when the water supply unit is operating and the nozzle is expelling water into the interior of the insect cage.

An embodiment is the insect breeding device 100A, 100B, 100C, 100D according to the invention, wherein the first pipe 102, 102b of water supply unit 101a-c, 500 is provided with a third driver 102a and a first valve 103C positioned downstream from the third driver 102a when a flow of liquid towards the at least one insect cage 100 during operation of the water supply unit 101a-c, 500 is considered, and wherein the first pipe 102, 102b is further provided with a branching opening 103D connected to branch pipe 102A, the branching opening 103D positioned downstream from the first valve 103C when a flow of liquid towards the at least one insect cage 100 during operation of the water supply unit 101a-c, 500 is considered, wherein branch pipe 102A comprises a second valve 103B.

An embodiment is the insect breeding device 100A, 100B, 100C, 100D according to the invention, wherein the first pipe 102, 102b (FIG. 1, 2) is provided with a third valve 103A which is configured such that during operation of water supply unit 101a, 101b, 101c the third valve 103A opens when the first valve 103C is in open position and the second valve 103B is in closed position, and the third valve 103A closes when the first valve 103C is in closed position and the second valve 103B is in open position. Optionally, the third valve 103A is a spring valve. Such as spring valve operates passively under influence of pressure exerted on the valve and therewith exerted on the pivot(s) with which the spring valve is pivotally connected to the interior side of the first pipe 102.

An embodiment is the insect breeding device 100A, 100B, 100C, 100D according to the invention, wherein the first pipe 102, 102b is provided with a spring valve 103A pivotally connected with the interior side of the first pipe 102, 102b via pivot 103, the spring valve 103A configured such that during operation of water supply unit 101a, 101b, 101c the spring pivotally opens the first pipe 102, 102b in the direction from the proximal end of the first pipe 102, 102b relative to the third driver 102a to the distal end of the first pipe 102, 102b where nozzle 106, 106A, 106B is connected with the first pipe 102, 102b, when the first valve 103C is in open position and the second valve 103B is in closed position, such that liquid is delivered inside the at least one insect cage 100.

An embodiment is the insect breeding device 100A, 100B, 100C, 100D according to the invention, wherein the spring valve 103A is configured to open, when in closed position, when a liquid pressure in the first pipe 102, 102b of at least 4 bar is exerted onto the closed spring valve, and to close, when in open position, when a liquid pressure in the first pipe 102, 102b of 3.5 bar or less is exerted onto the open spring valve, during operation of the water supply unit 101a, 101b, 101c, 500.

An embodiment is the insect breeding device 100A, 100B, 100C, 100D according to the invention, wherein the third driver 102a is a third pump 102a configured to provide liquid in the first pipe 102, 102b at a pressure of at least 4.5 bar, in particular 5-6 bar, during operation of the water supply unit 101a, 101b, 101c, 500, when the first valve 103C is in open position and the second valve 103B is in closed position.

An embodiment is the insect breeding device 100A, 100B, 100C, 100D according to the invention, wherein the surface area of the cross section of the second pipe 102A is such that during operation of the water supply unit 101a, 101b, 101c, 500 the liquid pressure in first pipe 102, 102b is less than 2 bar, in particular 0.8 to 1.2 bar, more in particular atmospheric pressure, when the first valve 103C is in closed position and the second valve 103B is in open position, such that spring valve 103A is in closed position.

An embodiment is the insect breeding device 100A, 100B, 100C, 100D according to the invention, wherein the first pipe 102, 102b is provided with a first pressure gauge 104 in a portion of the first pipe 102, 102b defined between the first valve 103C and the spring valve 103A.

An embodiment is the insect breeding device 100A, 100B, 100C, 100D according to the invention, wherein the water supply unit 101a, 101b, 101c, 500 is further provided with a sensor system comprising a first sensor 112d provided to the second pipe 112 and for measuring air humidity in the conditioned air in air flow b' provided to the insect cage 100 and entering said insect cage through second opening 112a, and comprising a second senor 113d provided to the third pipe 113 and for measuring air humidity in air flow b''' of the conditioned air exiting the insect cage 100 through third opening 113a, the first sensor 112d and the second sensor 113d both connected to the first valve 103c and to the second valve 103B and to the third valve 103A and optionally to the third driver 102a, for controlling the first valve 103C, the second valve 103B, the third valve 103A and optionally the third driver 102a, or the first sensor 112d and the second sensor 113d both connected to the first valve 103c, to the second valve 103B and optionally to the third driver 102a, when the third valve 103A is a spring valve 103A, for controlling the first valve 103C, the second valve 103B and optionally the third driver 102a.

An embodiment is the insect breeding device 100A, 100B, 100C, 100D according to the invention, comprising at least one insect cage 100, wherein the sensor system is configured to maintain the relative air humidity of the conditioned air in the at least one insect cage 100 at a predetermined and constant value, or to maintain the absolute air humidity at an air temperature of between 25° C. and 38° C. and at atmospheric pressure of 1.0 bar of the conditioned air in the at least one insect cage 100, at a predetermined and constant value.

Thus, as said, the first pipe 102 is provided with a spring valve 103A near the distal end of first pipe 102, when the reservoir-for-providing-demineralized-water side of first pipe 102 is considered. The spring valve is in closed position, i.e. closing the first pipe 102, when the water pressure applied on the valve is less than 3 bar. The first pipe is provided with a controllable valve 103C for inducing a flow a of pressurized drinking water (pressure is about 5-6 bar) through the first pipe 102. When the water pressure in first pipe 102 increases upon opening valve 103C, water pressure exerted on spring valve 103A rises to 5-6 bar, such that spring valve 103A pivotally opens due to the pivot 103 connected to the inner wall of the first pipe 102. Opening spring valve 103A results in operation of the nozzle 106, such that drinking water is ejected through the nozzle arms 107A-107C and exiting at nozzle arm exits 108A-108C in the direction of side walls 109A, B, D. The first pipe 102 is connected to a branching pipe 102A downstream valve 103C when the position of the reservoir for providing a liquid (demineralized water) such as a tap or container, is considered. Branching pipe 102A is provided with valve 103B.

For insect breeding device 100A-C, during operation of the tap (source of drinking water comprised by the drinking water supply unit 101a-d, 500 and nozzle 106, pressurized insect drinking water at a pressure of 4-6 bar is pushed through the first pipe 102 as flow a upon opening of valve 103C, and entering the insect cage 100 through opening 105 and subsequently nozzle 106, 106A, 106B. The flow of insect drinking water is for example 21 l/min-25 L/min, such as about 25 L/min or about 21 L/min. For insect breeding device 100A, the drinking water is provided as a surface portion 111a, 111b, 111c of the side walls 109B, 109D, 109A covered with fine droplets of demineralized water. The demineralized water is sprayed through the openings 108A-C towards the side walls 109A, 109B, 109D by directing water jets a1, a2, a3 towards said side wall portions.

Once the side wall portions are sufficiently covered with water droplets, the valve 103C is closed, and valve 103B is opened. Herewith the pressurized drinking water in the first pipe 102 upstream of branching pipe 102A flows in branching pipe 102A such that the pressure on the drinking water inside first pipe 102 and in the nozzle 106 drops to 1 bar. Herewith, spring valve 103A shuts and blocks water flow through pipe 102; provision of drinking water inside the cage 100 is effectively blocked and halted.

For FIG. 1A-F, a second pipe 112 connects the second opening 112a of the insect cage 100 to a supply 112b of temperature-controlled- and relative air humidity-controlled conditioned air, the supply 112b, comprising a climate control system, and provided with driver 112c for driving the conditioned air stream b into and through insect cage 100 in the direction b' towards the opposite side wall 109D. For FIG. 1A-F, a third pipe 113 connects the third opening 113a of the insect cage 100 to an air outlet for allowing conditioned air blown into the cage through opening 112a to exit insect cage 100 in the direction b'' to b''' outwardly. During operation of the insect breeding device 100A-C, the climate conditions for the controlled conditioned air blown into the cage 100 by driver 112c, are a temperature of 30° C.-34° C., typically 31.5° C.-32° C., and a specific humidity of the air of 16-22 gr/kg conditioned air, relating to relative humidity of the air of between 48.5% and 83.4%. The (constant) flow of the climatized (conditioned) air through the cage and through opening 113a and pipe 113 outwardly, is maintained at a flow that allows for maintaining the temperature inside the cage constantly at 30° C.-34° C., typically at 31.5° C.-32° C., and that allows for maintaining the relative air humidity at between 48.5% and 83.4%, typically between 48.5% and 74.4%. The climate control system of conditioned air supply 112b (air conditioning unit 112b) is configured to controllably provide the at least one insect cage 100 with an air flow b through the cage of between 10 m³/hour and 200 m3/hour, preferably about 100 m³/hour, more preferably about 45 m³/hour. The air flow through the cage is selected such that relative air humidity inside the cage is maintained within the indicated values. Furthermore, the air flow through the cage is selected such that the water droplets sprayed in zones 111a-c of side walls 109A, B, D (FIG. 1A, B), zone 111 of a portion of side walls 109A, B, D and a portion of bottom floor 109E (FIG. 1C, D, E, F), are minimally evaporating over time under influence of the flow b' to b'' of conditioned air through the cage.

For insect breeding device 100A-C, at the start of an insect breeding cycle, when breeding of black soldier flies is considered, for example a batch of about 44.000 pupae are provided onto surface portion 114 of bottom floor 109E of cage 100. In the time window between the provision of the pupae into the insect cage and subsequent emergence of the flies (typically taking hours to a day), the insects do not yet consume water. Since the pupae at first do not require and consume drinking water, and since the number of emerged flies is starting to accumulate the first few hours, e.g. up to 4 hours after provision of the pupae in the cage, water consumption is relatively limited in this time span. Therefore it suffices when the valve 103C is operated and opened for about 400-1000 msec (milliseconds) in intervals of up to 30 minutes-2 hours. The amount of available drinking water provided as droplets on the indicated interior surface areas of the insect cage requires replenishment mainly due to evaporation of water, and to a lesser extent to the water consumption by the early emerging flies. Then, during the next 4 hours up to three-four days, such as up to two days, all flies have emerged and drinking water consumption is at its maximum. During this time interval, when all flies have emerged, the valve 103C is operated and opened for about 1250 msec to 2500 msec in intervals as short as 5 min-20 min. This way, consumption of water by the flies and evaporation of drinking water is sufficiently and efficiently compensated for, while at the same time the amount of sprayed water is such that the drinking water adheres to the indicated side wall surface areas without flowing downward and onto the bottom floor. Therewith, wetting of the bottom floor, occurrence of pools of water coming with the risk of drowning flies, and wetting pupae that did not yet emerge is prevented. Avoidance of drown flies and avoidance of wetted and therewith decomposing pupae or pupae remains after emergence of the flies, avoids the built up of smelling bodies inside the insect cage. Such smelling bodies would otherwise serve as a source of olfactory trigger for gravid female flies, allowing these flies to lay eggs on/in dead flies and pupae (remains). Thus, keeping pupae (remains) dry and keeping flies from drowning contributes to optimal collection of eggs in the ovisite 202 located in the door opening covered with door 120. Furthermore, the nozzles 106, 106A and 106B of insect breeding devices 100A-C are configured such that drinking water is not supplied at or near the ovisite. Therewith, the eggs laid in the ovisite are prevented from becoming wetted, which would otherwise result in damaging and decomposing and even killing of the eggs, or the embryos there inside.

The drinking water flows from the reservoir of drinking water such as a vessel or a tap through the first pipe 102 into the nozzle (arrow a), positioned inside the at least one insect cage, in order to supply the inner surface of the insect cage with a mist or droplets of insect drinking water, adhering to said surface. The water jets exiting the nozzle exits have a velocity such that water does not contact the insect cage bottom floor, though arrives at the indicated spots on the side walls of the insect cage.

The pipe 102 connected to the insect cage 100 of breeding device 100A-C further comprises a pressure gauge, for measuring and controlling the insect drinking water pressure downstream valves 103B and 103C, and upstream spring valve 103A. During the interval in between two flushes of drinking water into the interior of the insect cage, valve 103B is closed, valve 103C is closed, and valve 103A is closed. To prevent the building up of pressure in pipe 102 to an extent that spring valve 103A would open to some extent, resulting in leakage of water droplets onto the bottom floor of the insect cage by gravitation, pressure gauge measures the water pressure and valve 103B is temporarily opened to release pressure again.

An example of such an insect breeding device of the invention is the insect breeding device 100B comprising at least one insect cage 100; comprising a nozzle 106A, coupled to the first pipe 102 through opening 105, positioned inside the at least one insect cage configured to deliver the demineralized water to the interior of the at least one insect cage. The nozzle 106A is a 75% disc nozzle, meaning that for the disc nozzle a disc portion of 90° is omitted. The omitted part of the disc nozzle is the part that would otherwise point to the fourth side wall 109C of the insect cage, where the ovisite is located and where pupae are deposited. The remaining 270° disc nozzle 106A is configured to wet side wall portion 111 of side walls 109A, B, D. The nozzle 106A provides water jets c when the water supply unit 101 is in operation and valves 103A and 103C are opened and valve 103B is closed. As said, the bottom floor 109E comprises bottom floor portion 114 that remains dry under influence of the operating nozzle 106A, due to the absence of the nozzle disc portion of 90°. Thus, also wetting of pupae is prevented, or wetting of pupae remains after emergence of the flies. The insect breeding device 100B is further provided with light source 110 near the top side 109F of the insect cage 100. Light from above stimulates the flies to gather in the upper portion of the insect cage, at the side wall portions where drinking water is provided. This reduces the risk for drowning flies, may accidentally drinking water form a pool at the bottom floor.

Turning to FIG. 1E, F, displaying insect breeding device 100C comprising drinking water supply unit 101, the fluid nozzle 106B can be a three quarter-cone nozzle 106B. The nozzle 109B is for example positioned at the distal end of a pipe 102 connecting the nozzle and the reservoir for providing a liquid, such as a tap. The opening 105 is here provided in the bottom floor 109E of the insect cage 100. The position of the 75% conical nozzle inside the insect cage is such that in operation the surface of the inner side of the insect cage is only partially contacted with the drinking water, i.e., expelled at for example a pressure of about 4-5 bar, for example for about 1000-2000 msec, at a speed of between about 150 liter/minute and 3500 liter/minute, preferably between 300 liter/minute and 2500 liter/minute, more preferable between 500 liter/minute and 2000 liter/minute, such that for example the insect cage is sufficiently provided with a volume of insect drinking water when the time interval between two deliveries of drinking water is about 200 sec-5000 sec, or 400 sec-2500 sec, when the insect cage has an inner volume of about between 100.000 cm$^3$ and 1.000.000 cm$^3$, preferably about 900.000 cm$^3$.

In one embodiment, the insect breeding device 100A-C of the present invention comprises a single nozzle 106, 106A, 106B positioned centrally in the inner volume of the insect cage 100. The nozzle is coupled to a rigid pipe or tube 102 for example made of metal or a polymer, said pipe or tube entering the cage inner volume either through the top wall 109F of the insect cage, from above, or through opening 105 in the bottom floor 109E of the insect cage, from below. Alternatively, the pipe or tube 102 enters the insect cage through an opening in a side wall 109A-D of the cage. Positioning the nozzle in the middle of the insect cage volume contributes to the efficiency of the provision and spreading of insect drinking water at the side wall inner surfaces when side walls 109A, B, D are considered. In one embodiment, the insect cage comprises at least two nozzles, preferably two nozzles positioned off center in the inner volume of the insect cage, for example at positions in the bottom floor located between 25% and 75% of the depth of the insect cage (determined by the distance between side wall 109C and 109D). In this arrangement the two nozzles in operation during a cycle of providing drinking water droplets at the side wall surfaces, generates a cyclone of drinking water such that also the top wall 109F is provided with a mist of fine water droplets adhering to the top wall surface, and such that also the bottom floor portion other than the bottom floor portion 114, is wetted by water droplets. Herewith, the area on which drinking water is provided to the flies is optimized.

Preferably, the insect cage 100 has a block shape with rounded corners. Sharp edges between the openings 105, 112a, 113a and the top wall and bottom floor of the cage are prevented, as well as the presence of any recess or ridge in the side of the opening. It appears that gravid female insects, e.g. gravid female black soldier flies, are in this embodiment prevented from deposition of their eggs in the opening or close proximity of the opening, since the provision of a perceived shelter, for example under a ridge, in a recess, in the opening below floor level, etc., for the eggs is prevented.

In an embodiment of the present invention, the water supply unit 101 of insect breeding device 100A-C comprises a first valve 103A, which is a passively operating pressure driven spring valve, coupled to a first opening 105 of the insect cage and to the distal end of pipe 102 relative to the location of the reservoir for providing a liquid (FIG. 2), configured to open or close the first opening, and a first valve 103C, located at the proximate end of the pipe 102 relative to the reservoir for providing a liquid such as a water tap, configured to open or close pipe 102 and to allow drinking water pressurized at 5-6 bar to flow from the reservoir for providing a liquid, e.g. a tap providing demineralized water, towards and through nozzle 106, 106A, 106B. Further, the water supply unit 101 comprises a second valve 103B located in branch pipe 102A connected to pipe 102 therewith providing pipe 102 with a branch.

In one embodiment, the insect breeding device 100A-C, comprises a controller 104 connected to the first valve 103C and the second valve 103B, wherein the controller can switch between a first state and a second state. In the first state the first and second valves 103A, 103C are closed and the second valve 103B is open. This first state represents when the insect cage does not require supply of drinking water, and it is not possible to deliver or expel demineralized water into the insect cage. Water pressure in pipe 102 is lower than about 3 bar, i.e. about 1 bar, such that the spring valve 103A is not opened, since the pressure threshold for opening valve 103A is exerting a water pressure of at least 4 bar. In the second state, the first valve 103A, the spring valve, is open and the second valve 103C is open and the second valve 103B is closed. In the second state the insect drinking water (demineralized water from the reservoir for providing a liquid such as a tap) is delivered into the insect cage. In the second state, controller 104 has opened valve 103C and closed valve 103B, such that the pressurized water from the reservoir for providing a liquid, such as a demineralized water tap, at 5-6 bar, flows through pipe 2, the water exerting sufficient pressure over the threshold of 4 bar, to open spring valve 103A, such that the drinking water is supplied inside the insect cage.

Figure 2:
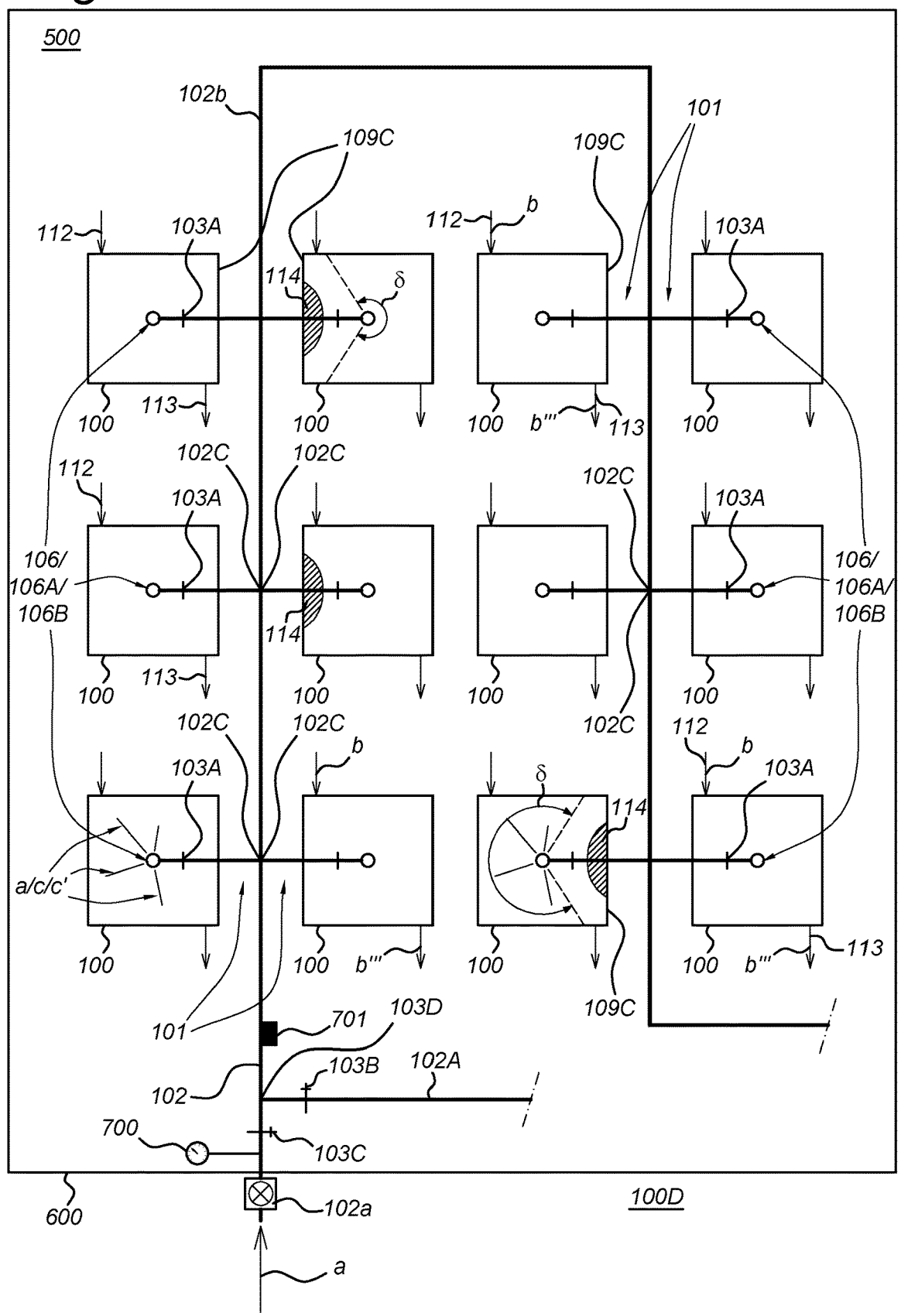
FIG. 2 illustrates an embodiment of an insect breeding device of the invention, the insect breeding device comprising a breeding room encompassing the insect breeding device, and the insect breeding device comprising a multitude of insect cages. The insect breeding device comprises a cluster of cages, each cage provided with a drinking water supplying nozzle.

FIG. 2 displays an insect breeding device 100A-C comprising multiple insect cages 100 each provided with a water supply unit 101, the insect breeding device further comprising a climate room 600 surrounding the insect cages. Shown are the controller comprising pressure gauge 700, configured to control and operate the valves 103A (when valves are in an embodiment not passively opening when provided as spring valves), 103B and 103C, now for multiple cages simultaneously when operating the valves 103A, 103B and 103C is considered (if valve 103A is not a passively operating spring valve). Alternatively, in an embodiment wherein the valve 103A is a spring valve, such as here above outlined, the controller 700 controls and operates valves 103B and 103C. For the purpose of venting the drinking water supply unit(s) 101 of the insect breeding device 100A-C, the pipe 102 is provided with a vent, preferably located at a highest part of the pipe 102 relative to the horizontal such that efficient venting occurs.

An embodiment is the insect breeding device 100D according to the invention, wherein the at least one insect cage 100 is a cluster of insect cages 100 comprising two or more insect cages, such as 48-256 insect cages, wherein the first pipe 102, 102b of water supply unit 500 comprises branch points 102c connected to water supply unit branches 101 comprising the third valve 103A such as the spring valve 103A and the nozzle 106, 106A, 106B located inside the individual insect cages, the insect breeding device further comprising a climate room 600 enclosing the at least one insect cage 100 and a portion of the water supply unit 101 encompassing at least the portion of the first pipe 102b comprising the branch points 102c and the water supply unit branches 101.

For example, the insect breeding device 100A-C may comprise about one hundred to 1000 horizontally and vertically stacked insect cages in an insect farming room 600 such as a climate room 600 for breeding insects, and breeding cycles including multiple times disposal of drinking water inside the cages can be performed without the need to displace the insect cages. Typically, the insect breeding device may comprise two-ten insect cages stacked vertically, and typically tens to hundreds of insect cages stacked horizontally, such as about 20-500 insect cages.

Typically, stacked insect cages provided with the insect breeding device have round-corners on the inner surface of insect cages (hereafter referred to as "round cornered cages"). Such round cornered cages contribute to preventing gravid female insects from ovipositioning at the corners of the insect cages.

An embodiment is the insect breeding device 100D according to the invention, comprising at least one insect cage 100, wherein the first pipe 102, 102b of water supply unit 500 comprises a second pressure gauge 700 between the third driver 102a and the first valve 103C, and/or at least one vent 701 downstream from the first valve 103C and the second valve 103B.

An embodiment is the insect breeding device 100A-D according to the invention, comprising at least one insect cage 100, wherein the second pressure gauge 700 further comprises
  a controller 700 connected to the first valve 103C and to the second valve 103B and the third pump 102a, wherein the controller 700 is arranged to switch between a first state and a second state; wherein
    in the first state the first valve 103C is closed, the second valve 103B is open and the third pump 102a is optionally switched off,
  in the second state, the first valve 103C is open and the second valve 103B is closed, and the third pump 102a is switched on, if previously switched off.

An embodiment is the insect breeding device 100A-D according to the invention, wherein the second pressure gauge 700 further comprises
  a controller 700 connected to the first valve 103C, to the second valve 103B, to the third valve 103A and to the third pump 102a, wherein the controller 700 is arranged to switch between a first state and a second state; wherein
    in the first state the first valve 103C and the third valve 103A are closed, the second valve 103B is open and the third pump 102a is optionally switched off,
    in the second state, the first valve 103C and the third valve 103A are open and the second valve 103B is closed, and the third pump 102a is switched on, if previously switched off when the third pump 102a is switched off in the first state.

An embodiment is the insect breeding device 100A-D according to the invention, wherein the controller 700 is further arranged to maintain the second state for a period between 300 milliseconds to 5000 milliseconds, such as between 500 milliseconds and 2500 milliseconds.

An embodiment is the insect breeding device 100A-D according to the invention, wherein the controller 700 is further arranged to maintain the first state for a period between 1 minute and 6 hours, preferably between 3 minutes and 3 hours, more preferably between 5 minutes and 2 hours.

An embodiment is the insect breeding device 100A-D according to the invention, wherein the flow of liquid through the first pipe 102, 102b is between 10 L/min and 50 L/min, preferably between 15 L/min and 40 L/min, more preferably between 21 L/min and 25 L/min, when the first valve 103C is open and the second valve 103B is closed. The liquid is for example tap water and the liquid is preferably demineralized water, for example when the insect breeding device is applied for breeding insects such as black soldier fly.

The round cornered cages that are provided with the insect breeding device are preferably produced by rotation molding. Rotation molding provides cages with an inner surface of the side walls, top and floor that is particularly smooth. Such smooth surfaces contribute to the cleaning efficiency of the insect breeding device.

In one embodiment, the round cornered cages provided with the breeding device of the invention are made of a polymer or a polymer blend, preferably the cages are made of a polymer blend comprising polyethylene. In one embodiment, the round cornered cages provided with the breeding device of the invention are made of polyethylene. In one embodiment, said round cornered cages are made by rotation molding a blend of polyethylene, according to the invention. In one embodiment, said round cornered cages are made by rotation molding medium density polyethylene, according to the invention. In one embodiment, the round cornered cages provided with the breeding device of the invention are made of polypropylene. Insect cages comprised by the insect breeding device of the invention, which are made of such a material, have good water droplet adherence properties, at the climate conditions applied during an insect breeding cycle, and size of droplets remains sufficiently small at e.g. the side walls of the cage and occasionally at the bottom floor of the cage, such that a risk for drowning insects is limited.

Typically, a plurality of insect cages provided with the insect breeding device of the present invention have an inner size suitable for farming between 500 and 50.000 adult insects, such as between 1.000 and 20.000 adult insects. Typically, the round cornered cages for farming adult insects such as black soldier flies and for collecting the eggs derived therefrom, have inner dimensions of between 30 cm and 300 cm (width), between 50 cm and 400 cm (depth), and between 10 cm and 200 cm (height), for example between 30 cm and 220 cm (width), between 50 cm and 300 cm (depth), and between 10 cm and 150 cm (height), or for example between 30 cm and 150 cm (width), between 50 cm and 200 cm (depth), and between 10 cm and 100 cm (height). Preferably, such round cornered cages provided with the insect breeding device of the present invention are substantially block shaped, typically with the following dimensions: about 120 cm (width), about 50 cm (height), 170 cm (depth), or for example about 160 cm (width), about 90 cm (height), 220 cm (depth). Preferred is a cage with a width of about 110 cm, a height of about 70 cm and a depth of about 160 cm, or for example a width of about 140 cm, a height of about 80 cm and a depth of about 200 cm.

Conventional provision of the insect cages by drinking water multiple times per day during an insect breeding cycle one by one would require about between 2 minutes up to 4 minutes per cage, and typically about 3 minutes on average of labor. Applying the automated and controllable insect breeding device of the present invention reduces the required time for provision of a single insect cage with multiple doses of drinking water per 1-2 hours, or even per 5-20 minutes, to between 500 msec and 2500 msec, on average, for provision of drinking water to for example between 4 and 20 cages simultaneously.

One of the many advantages of the insect breeding device of the present invention is the safety that is provided to workers involved in the farming of insects including provision of insect cages with drinking water multiple times during a cycle of breeding, with regard to the reduced risk of contaminating a colony of insects bred in a cage.

Before an insect cage is used in a first or subsequent round of an insect breeding cycle starting from the pupae stage up to death of the adult insect after mating and the gravid female insects having ovipositioned, the applied insect cage preferably has a dry inner surface cleared from droplets of fluid such as water. Referring to FIG. 1, the insect breeding device further comprises a gas drying apparatus drying the interior of each insect cage after the insect cages have been cleaned. Preferably, the interior of the insect cages is dried with air after cleaning of the insect cages. In an embodiment the insect breeding device 100A-C further comprises of a ventilator 112c and optionally an air heater (not shown). The ventilator 112c generates a gas flow, where the gas is then optionally heated at the heater. The gas or the heated gas is then transferred through pipe 112 to supply air to the insect cages 100 through opening 112a of the insect cage. The opening 113a of the insect cage is used to allow the gas to exit the cage. It is appreciated that the gas drying apparatus is the same apparatus as applied for providing the interior of the insect cage with conditioned air at predetermined temperature and relative humidity of the air, optimal for flies emerging from pupae and the subsequent mating and ovipositioning.

Summarizing these embodiments of the invention, an embodiment is thus the insect breeding device 100A-D according to the invention, wherein the at least one insect cage 100 has a substantially block shape having rounded corners in the inner surface of the cage.

An embodiment is the insect breeding device 100A-D according to the invention, wherein the at least one insect cage 100 is manufactured using rotation molding of a polymer blend, preferably comprising polyethylene.

An embodiment is the insect breeding device 100A-D according to the invention, wherein the at least one insect cage 100 is further configured to have inner dimensions of a width between 30 cm and 250 cm, a depth between 50 cm and 300 cm and a height between 10 cm and 160 cm, for example a width between 30 cm and 150 cm, a depth between 50 cm and 200 cm and a height between 10 cm and 60 cm.

An embodiment is the insect breeding device 100A-D according to the invention, wherein the first opening 105 of the at least one insect cage 100 is located in the bottom floor 109E of the insect cage, or is located in the top wall 109F of the insect cage.

An embodiment is the insect breeding device 100A-D according to the invention, wherein the nozzle 106, 106A, 106B is configured to have a spray angle between 180 degrees and 270 degrees and during operation of the water supply unit 101a-c, 500 is configured to spray liquid in directions other than towards the fourth side wall 109C of the at least one insect cage 100 and other than towards the bottom floor portion 114 of the insect cage 100.

An embodiment is the insect breeding device 100A-D according to the invention, wherein the nozzle 106, 106A, 106B is arranged to be positioned centrally in the inner volume of the at least one insect cage 100.

An embodiment is the insect breeding device 100A-D according to the invention, wherein the at least one insect cage 100 comprises a further nozzle, the nozzles being positioned off-center, in the inner volume of the at least one insect cage.

An embodiment is the insect breeding device 100A-D according to the invention, comprising two insect cages 100 stacked horizontally or vertically with each other.

An embodiment is the insect breeding device 100A-D according to the invention, comprising two-eight hundred insect cages 100 stacked horizontally with each other, and/or two-fifteen insect cages 100 stacked vertically with each other, for example five-three hundred fifty horizontally stacked insect cages and/or three-seven vertically stacked insect cages. A typical stack of insect cages comprised by the insect breeding device of the invention encompasses 1-6 cages (height) times 2-45 cages (length) times 2-100 (breadth) stacked cages. A stack of cages may comprises 10, 100, 1000, 5000 cages, comprised by the insect breeding device, according to the invention.

While the invention has been described in terms of several embodiments, it is contemplated that alternative embodiments, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims. The embodiments of the invention described herein can operate in combination and cooperation, unless specified otherwise.

The invention claimed is:

1. An insect breeding device comprising
at least one insect cage, the insect cage having a bottom floor, a first side wall, a second side wall, a third side wall, a fourth side wall opposite to first side wall and a top wall;
a water supply unit provided with:
a reservoir for providing a liquid;
a first pipe connected to the reservoir for receiving the liquid from the reservoir, wherein the first pipe enters the at least one insect cage through a first opening in the at least one insect cage;
a nozzle, coupled to the first pipe, positioned inside the at least one insect cage and configured to deliver the liquid to an interior of the at least one insect cage on at least one of the first side wall, the second side wall, the third side wall, the top wall and a portion of the bottom floor apart from a bottom floor portion, which bottom floor portion is located adjacent to the fourth side wall,
wherein the fourth side wall of the at least one insect cage is provided with a cage access opening for receiving an ovisite, and an openable door for covering said cage access opening and the ovisite, and when the insect breeding device is in use, the ovisite is positioned above the bottom floor portion of the bottom floor of the at least one insect cage, such that during operation of the water supply unit the ovisite and the bottom floor portion remain dry.

2. The insect breeding device of claim 1, wherein the nozzle is configured to deliver liquid on at least the first side wall, the second side wall and the third side wall.

3. The insect breeding device according to claim 1, wherein the at least one insect cage is provided with a second pipe connected to a supply of conditioned air for receiving the conditioned air and for delivery of the conditioned air inside the insect cage during operation of the insect breeding device, the second pipe connected to a second opening in the top wall in proximity of the fourth side wall, or in the fourth side wall, of the at least one insect cage, and the second pipe provided with an air conditioning unit for conditioning of the air temperature and conditioning of the relative humidity of the air before delivery of the conditioned air inside the at least one insect cage during operation of the insect breeding device, and a first driver for transport and delivery of the conditioned air through the second pipe and inside the at least one insect cage through the second opening; and wherein the at least one insect cage is provided with a third pipe for receiving the conditioned air delivered by the second pipe during operation of the insect breeding device, connected to a third opening in the top wall in proximity of the first side wall, or in the first side wall, of the at least one insect cage,
wherein during operation of said insect breeding device the first driver pumps between 10 m3/hour and 200 m3/hour conditioned air inside the at least one insect cage,
wherein the temperature of the conditioned air is 29° C.-35° C., and/or the relative air humidity of the conditioned air is 45%-90%.

4. The insect breeding device according to claim 3, wherein the air conditioning unit is an absolute air humidity control unit which is configured to controllably provide the at least one insect cage with an air flow of conditioned air through the at least one insect cage with an absolute air humidity of between 5 gram H2O/kg air and 46 gram H2O/kg air at an air temperature of between 25° C. and 38° C. at atmospheric pressure of 1.0 bar.

5. The insect breeding device according to claim 3, wherein the water supply unit is further provided with a sensor system comprising a first sensor provided to the second pipe and for measuring air humidity in the conditioned air in air flow provided to the insect cage and entering said insect cage through second opening, and comprising a second sensor provided to the third pipe and for measuring air humidity in air flow of the conditioned air exiting the insect cage through third opening; the first sensor and the second sensor both connected to the first valve and to the second valve and to the third valve for controlling the first valve, the second valve and the third valve, or the first sensor and the second sensor both connected to the first valve and to the second valve when the third valve is a spring valve, for controlling the first valve and the second valve.

6. The insect breeding device according to claim 5, wherein the sensor system is configured to maintain the relative air humidity of the conditioned air in the at least one insect cage at a predetermined and constant value, or to maintain the absolute air humidity at an air temperature of between 25° C. and 38° C. and at atmospheric pressure of 1.0 bar of the conditioned air in the at least one insect cage.

7. The insect breeding device according claim 1, wherein the nozzle is provided with three arms oriented in a plane, the three arms defining angles of 90° between a first arm and a second arm, and between the second arm and a third arm, and an angle of 180° between the first arm and the third arm pointing to the fourth side wall, each of the three arms having a fluid exit opening, the nozzle being configured to deliver water jets in directions over an angle of between 180° and 270° during operation of the insect breeding device, such that the water jets wet the first side wall, the second side wall and the third side wall of the at least one insect cage;
or
wherein the nozzle is a semi-circular disc nozzle covering 180° of a circular disc nozzle, or a three-quarter circular disc nozzle covering 270° of a circular disc nozzle, the nozzle being configured to deliver water jets in directions over an angle of 180° for the semi-circular disc nozzle and 270° for the three-quarter circular disc nozzle during operation of the insect breeding device, such that the water jets wet the first side wall, the second side wall and the third side wall of the at least one insect cage;

or wherein the nozzle is a semi-circle conical nozzle covering 180° of a conical nozzle, or a three-quarter circle conical nozzle covering 270° of a conical nozzle, the nozzle being configured to deliver water jets in directions over an angle of 180° for the semi-circle conical nozzle and 270° for the three-quarter circle conical nozzle during operation of the insect breeding device, such that the water jets wet the first side wall, the second side wall and the third side wall.

8. The insect breeding device according to claim 1, wherein the first pipe of water supply unit is provided with a third driver and a first valve positioned downstream from the third driver for a flow of liquid towards the at least one insect cage during operation of the water supply unit, and wherein the first pipe is further provided with a branching opening connected to a branch pipe, the branching opening positioned downstream from the first valve for a flow of liquid towards the at least one insect cage during operation of the water supply unit, wherein the branch pipe comprises a second valve.

9. The insect breeding device according to claim 8, wherein the first pipe is provided with a third valve which is configured such that during operation of water supply unit the third valve opens when the first valve is in open position and the second valve is in closed position, and the third valve closes when the first valve is in closed position and the second valve is in open position.

10. The insect breeding device according to claim 9, wherein the third valve is a spring valve pivotally connected with an interior side of the first pipe via pivot, the spring valve configured such that during operation of water supply unit the spring pivotally opens the first pipe in a direction from a proximal end of the first pipe relative to the third driver to a distal end of the first pipe where nozzle is connected with the first pipe, when the first valve is in open position and the second valve is in closed position, such that liquid is delivered inside the at least one insect cage.

11. The insect breeding device according to claim 10, wherein the spring valve is configured to open, when in closed position, when a liquid pressure in the first pipe of at least 4 bar is exerted onto the closed spring valve, and to close, when in open position, when a liquid pressure in the first pipe of 3.5 bar or less is exerted onto the open spring valve, during operation of the water supply unit.

12. The insect breeding device according to claim 9, wherein the third driver is a third pump configured to provide liquid in the first pipe at a pressure of at least 4.5 bar during operation of the water supply unit, when the first valve is in open position and the second valve is in closed position.

13. The insect breeding device according to claim 9, wherein a surface area of a cross section of the second pipe is such that during operation of the water supply unit a liquid pressure in the first pipe is less than 2 bar when the first valve is in closed position and the second valve is in open position, such that spring valve is in closed position.

14. The insect breeding device according to claim 9, wherein the first pipe is provided with a first pressure gauge in a portion of the first pipe defined between the first valve and the spring valve.

15. The insect breeding device according to claim 9, wherein the at least one insect cage is a cluster of insect cages comprising two or more insect cages, wherein the first pipe of water supply unit comprises branch points connected to water supply unit branches comprising the third valve and the nozzle located inside the insect cages, the insect breeding device further comprising a climate room enclosing the at least one insect cage and a portion of the water supply unit encompassing at least a portion of the first pipe comprising the branch points and the water supply unit branches.

16. The insect breeding device according to claim 15, wherein the first pipe of water supply unit comprises a second pressure gauge between the third driver and the first valve, and/or at least one vent downstream from the first valve and the second valve.

17. The insect breeding device according to claim 16, wherein the second pressure gauge further comprises
a controller connected to the first valve and to the second valve and to the third pump, wherein the controller is arranged to switch between a first state and a second state; wherein
in the first state the first valve is closed, the second valve is open and the third pump is switched off,
in the second state, the first valve is open and the second valve is closed, and the third pump is switched on.

18. The insect breeding device according to claim 16, wherein the second pressure gauge further comprises
a controller connected to the first valve, to the second valve, to the third valve and to the third pump, wherein the controller is arranged to switch between a first state and a second state; wherein
in the first state the first valve and the third valve are closed, the second valve is open and the third pump is switched off,
in the second state, the first valve and the third valve are open and the second valve is closed, and the third pump is switched on.

19. The insect breeding device according to claim 1, wherein the nozzle is configured to have a spray angle between 180 degrees and 270 degrees and during operation of the water supply unit is configured to spray liquid in directions other than towards the fourth side wall of the at least one insect cage and other than towards the bottom floor portion of the insect cage.

20. The insect breeding device according to claim 1, wherein the nozzle is arranged to be positioned centrally in an inner volume of the at least one insect cage.

* * * * *